United States Patent
Hopkins

(10) Patent No.: US 10,022,079 B2
(45) Date of Patent: Jul. 17, 2018

(54) SYRINGE SYSTEMS AND METHODS FOR BODILY FLUID COLLECTION AND SAMPLING

(71) Applicant: Michael Hopkins, Springboro, OH (US)

(72) Inventor: Michael Hopkins, Springboro, OH (US)

(73) Assignee: TRUE CONCEPTS MEDICAL TECHNOLOGIES, LLC, Springboro, OH (US)

(*) Notice: Subject to any disclaimer, the term of this patent is extended or adjusted under 35 U.S.C. 154(b) by 0 days.

(21) Appl. No.: 15/624,467

(22) Filed: Jun. 15, 2017

(65) Prior Publication Data

US 2017/0360342 A1 Dec. 21, 2017

Related U.S. Application Data

(60) Provisional application No. 62/350,341, filed on Jun. 15, 2016.

(51) Int. Cl.
*A61B 5/15* (2006.01)
*A61B 5/153* (2006.01)
*A61B 5/154* (2006.01)

(52) U.S. Cl.
CPC .... *A61B 5/150251* (2013.01); *A61B 5/15003* (2013.01); *A61B 5/153* (2013.01); *A61B 5/154* (2013.01); *A61B 5/150221* (2013.01); *A61B 5/150351* (2013.01); *A61B 5/150992* (2013.01)

(58) Field of Classification Search
CPC ................................. A61B 5/150251
See application file for complete search history.

(56) References Cited

U.S. PATENT DOCUMENTS

| | | |
|---|---|---|
| 4,340,068 A | 7/1982 | Kaufman |
| 9,155,495 B2 | 10/2015 | Bullington et al. |
| 2007/0073267 A1 | 3/2007 | Muller |
| 2010/0286609 A1 | 11/2010 | Mahurkar |
| 2011/0009830 A1 | 1/2011 | Kosinski et al. |
| 2012/0016313 A1 | 1/2012 | Nalesso et al. |
| 2012/0220950 A1 | 8/2012 | Carlyon |
| 2014/0163419 A1 | 6/2014 | Bullington et al. |

OTHER PUBLICATIONS

Thomas, Shane; International Search Report and Written Opinion of the International Searching Authority, issued in International Application No. PCT/US2017/037789; dated Sep. 6, 2017; 9 pages.
Thomas, Shane; International Search Report and Written Opinion of the International Searching Authority, issued in International Application No. PCT/US2017/037778; dated Sep. 6, 2017; 11 pages.

*Primary Examiner* — Daniel Cerioni
*Assistant Examiner* — Yasmeen S Warsi
(74) *Attorney, Agent, or Firm* — Ulmer & Berne LLP

(57) ABSTRACT

Embodiments of a syringe-based device for procuring bodily fluid samples can include a housing having a port that can be coupled to a lumen-defining device for receiving bodily fluids, an actuator mechanism retained at least partially within the housing, the actuator mechanism including a pre-sample reservoir, a plunger operably coupled with pre-sample reservoir, a plunger cap, a plunger tube, a valve, a plunger seal, an a selectively attachable collection vial for capturing a bodily fluid sample.

20 Claims, 26 Drawing Sheets

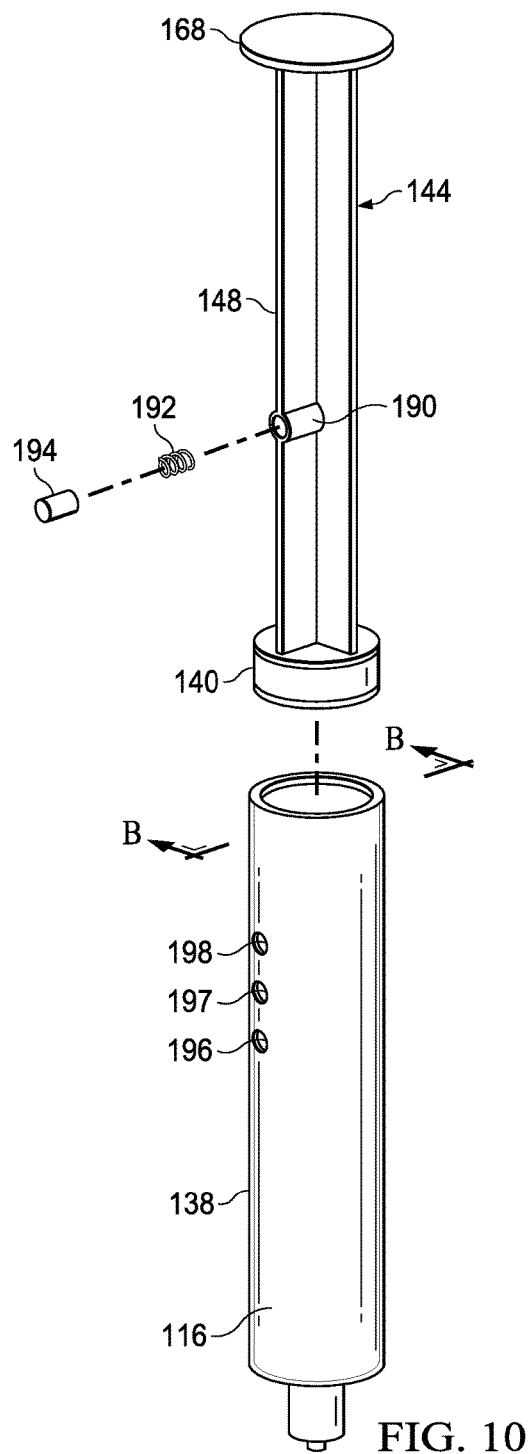
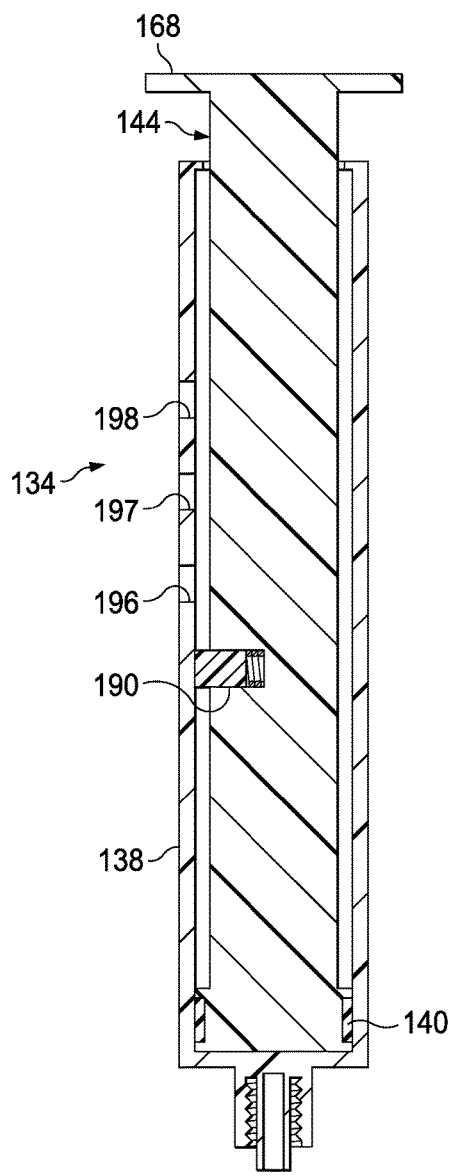
FIG. 10
FIG. 11

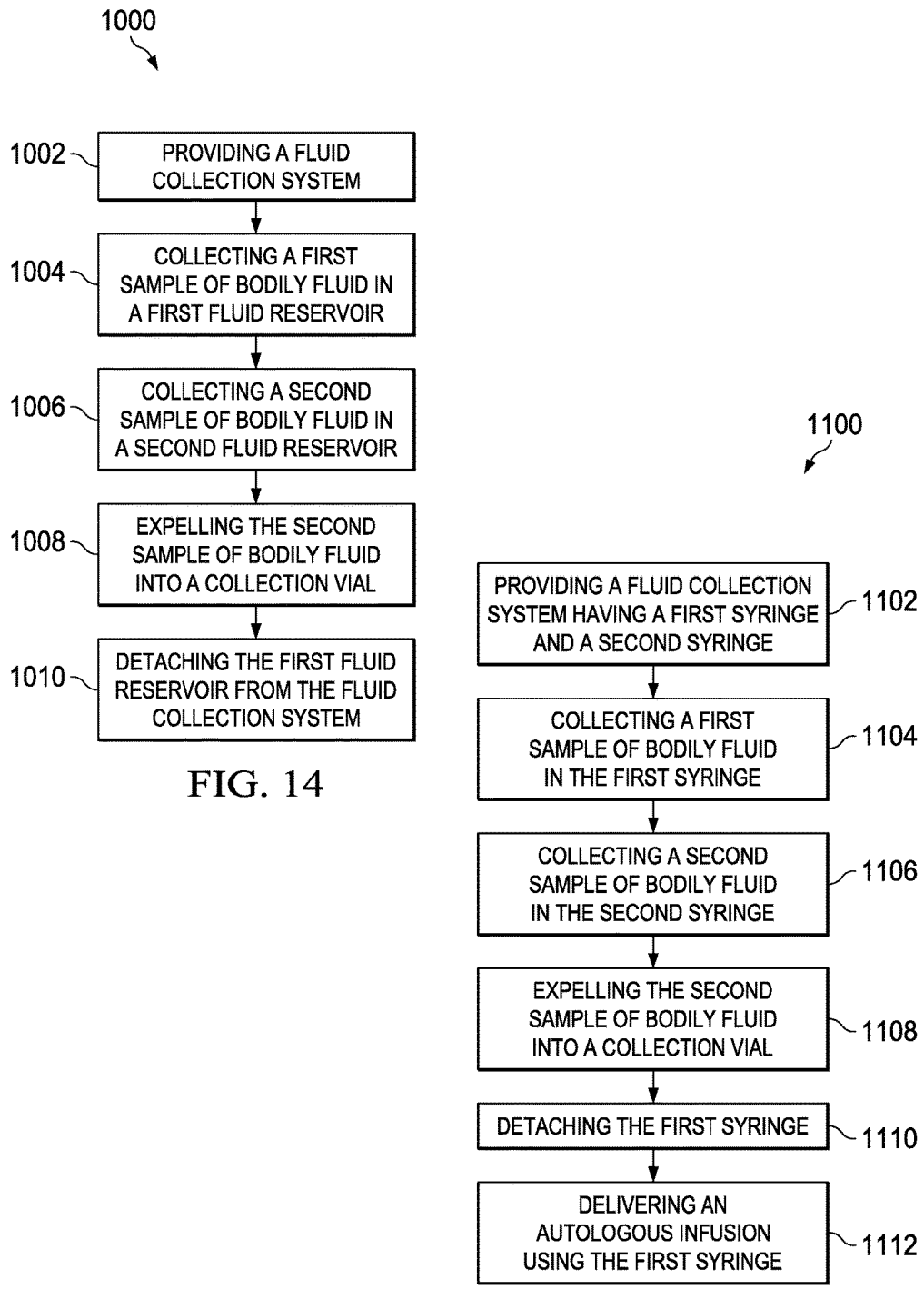

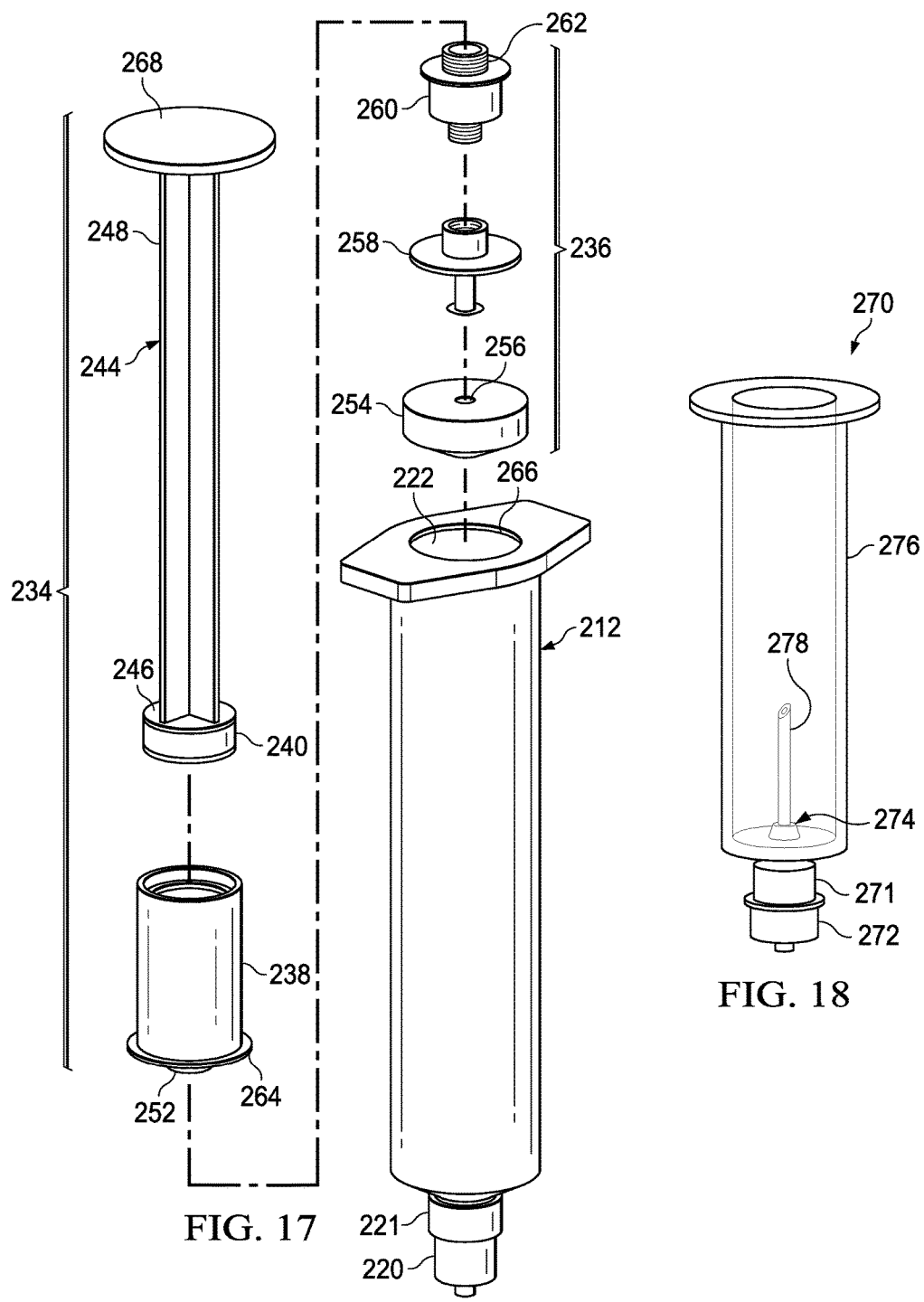

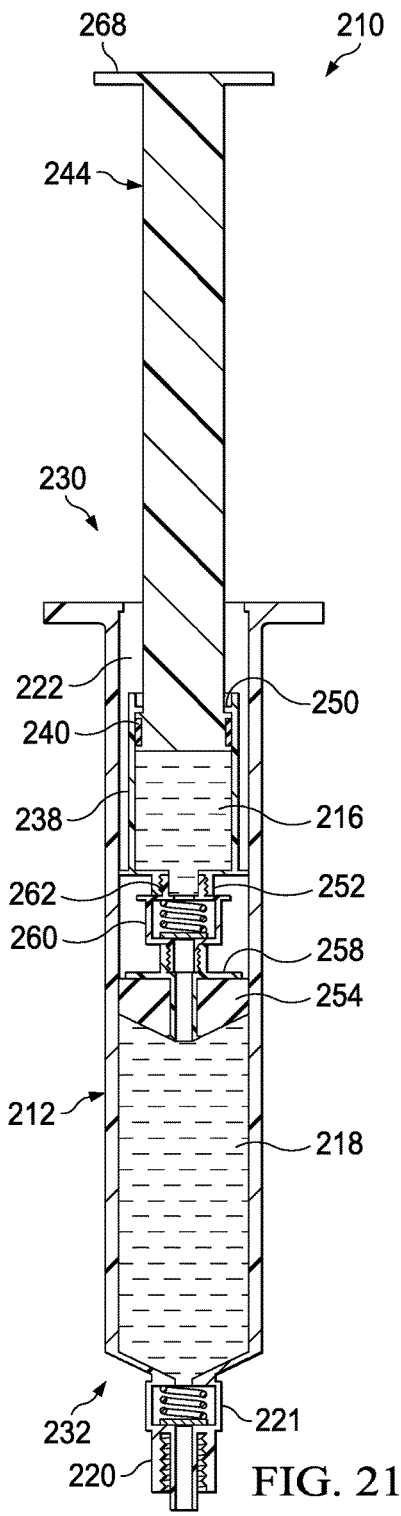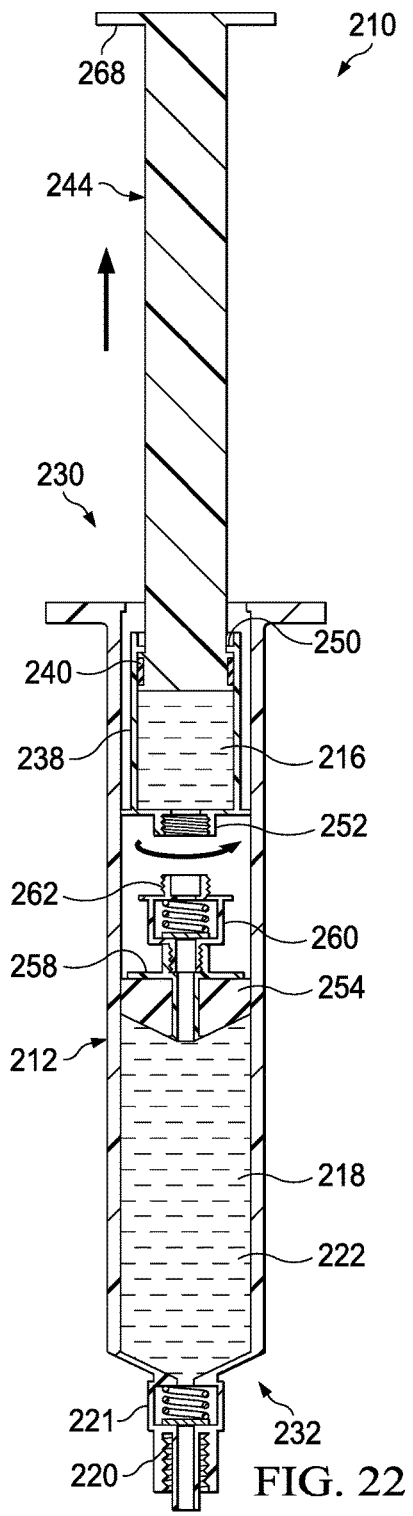

SYRINGE SYSTEMS AND METHODS FOR BODILY FLUID COLLECTION AND SAMPLING

REFERENCE TO RELATED APPLICATIONS

This application claims priority to U.S. Provisional Patent Application No. 62/350,341, filed Jun. 15, 2016, which is incorporated by reference herein in its entirety.

TECHNICAL FIELD

Embodiments of the technology relate, in general, to syringe technology, and in particular to syringe systems for the collection of bodily fluids including the collection of blood from about a Central Venous Catheter (CVC).

BACKGROUND

Health care practitioners routinely perform various types of tests on patients using bodily-fluids. In some instances, patient samples (e.g., bodily-fluids) are tested for the presence of one or more potentially undesirable microbes, such as bacteria, fungi, or yeast (e.g., *Candida*). Microbial testing may include incubating patient samples in one or more sterile vessels containing culture media that is conducive to microbial growth, real-time diagnostics, and/or PCR-based approaches. Generally, when such microbes are present in the patient sample, the microbes flourish over time in the culture medium. After a pre-determined amount of time (e.g., a few hours to several days), the culture medium can be tested for the presence of the microbes. The presence of microbes in the culture medium suggests the presence of the same microbes in the patient sample which, in turn, suggests the presence of the same microbes in the bodily-fluid of the patient from which the sample was obtained. Accordingly, when microbes are determined to be present in the culture medium, the patient may be prescribed one or more antibiotics or other treatments specifically designed to treat or otherwise remove the undesired microbes from the patient.

Patient samples, however, can become contaminated during procurement. One way in which contamination of a patient sample may occur is by the transfer of microbes (e.g., dermally or sub-dermally residing microbes), from saline associated with a CVC line flush, or from heparin associated with a CVC line flush. The transferred microbes may thrive in the culture medium and eventually yield a positive microbial test result, thereby falsely indicating the presence of such microbes in vivo. Such inaccurate results are a concern when attempting to diagnose or treat a suspected illness or condition. For example, false positive results from microbial tests may result in the patient being unnecessarily subjected to one or more anti-microbial therapies, which may cause serious side effects to the patient including, for example, death, as well as produce an unnecessary burden and expense to the health care system.

BRIEF DESCRIPTION OF THE DRAWINGS

The present disclosure will be more readily understood from a detailed description of some example embodiments taken in conjunction with the following figures:

FIG. 10 depicts an exploded view of pre-sample syringe having a pin and cylinder system that can permit clinician selection of a desired pre-sample volume according to one embodiment;

FIG. 11 depicts a cross-sectional view of the pre-sample syringe of FIG. 10, taken along reference line B-B;

FIG. 14 depicts a flow chart showing a method of using a fluid transfer device in accordance with one embodiment.

FIG. 15 depicts a flow chart showing a method of using a fluid transfer device to provide an autologous infusion in accordance with one embodiment.

FIG. 17 depicts an exploded view of the dual syringe blood collection system shown in FIG. 16;

FIG. 18 depicts a perspective view of a fluid transfer adapter for use with the dual syringe blood collection system shown in FIG. 16 according to one embodiment.

FIG. 21 depicts a cross-sectional view of the dual syringe blood collection system of FIG. 16, shown with a sample drawn into a second reservoir;

FIG. 22 depicts a cross-sectional view of the dual syringe blood collection system of FIG. 16, shown with the first reservoir selectively detached from the system;

DETAILED DESCRIPTION

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure.

Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment," or "in an embodiment" in places throughout the specification are not necessarily all referring to the same embodiment. Furthermore, the particular features, structures or characteristics may be combined in any suitable manner in one or more embodiments.

Described herein are example embodiments of apparatuses, systems, and methods for fluid collection. In one example embodiment, a dual syringe fluid collection system is provided that can isolate a contaminated pre-sample from an uncontaminated fluid sample for testing. In some embodiments, the dual syringe fluid collection system can include a pre-sample syringe that can be selectively detachable from the system. In some embodiments, a selectively detachable pre-sample syringe can be selectively detachable from the system and can be used to provide an autologous infusion back to the patient. Embodiments of a dual syringe fluid collection system can have a "closed system" configuration such that blood or fluid is not expelled through the distal port of the device. Some embodiments can include a fluid collection system having two or more one way valves to facilitate a closed system. Embodiments can include a fluid transfer adapter that can be selectively attached and/or is part of a unitary construction with the fluid collection system.

Figure 1:
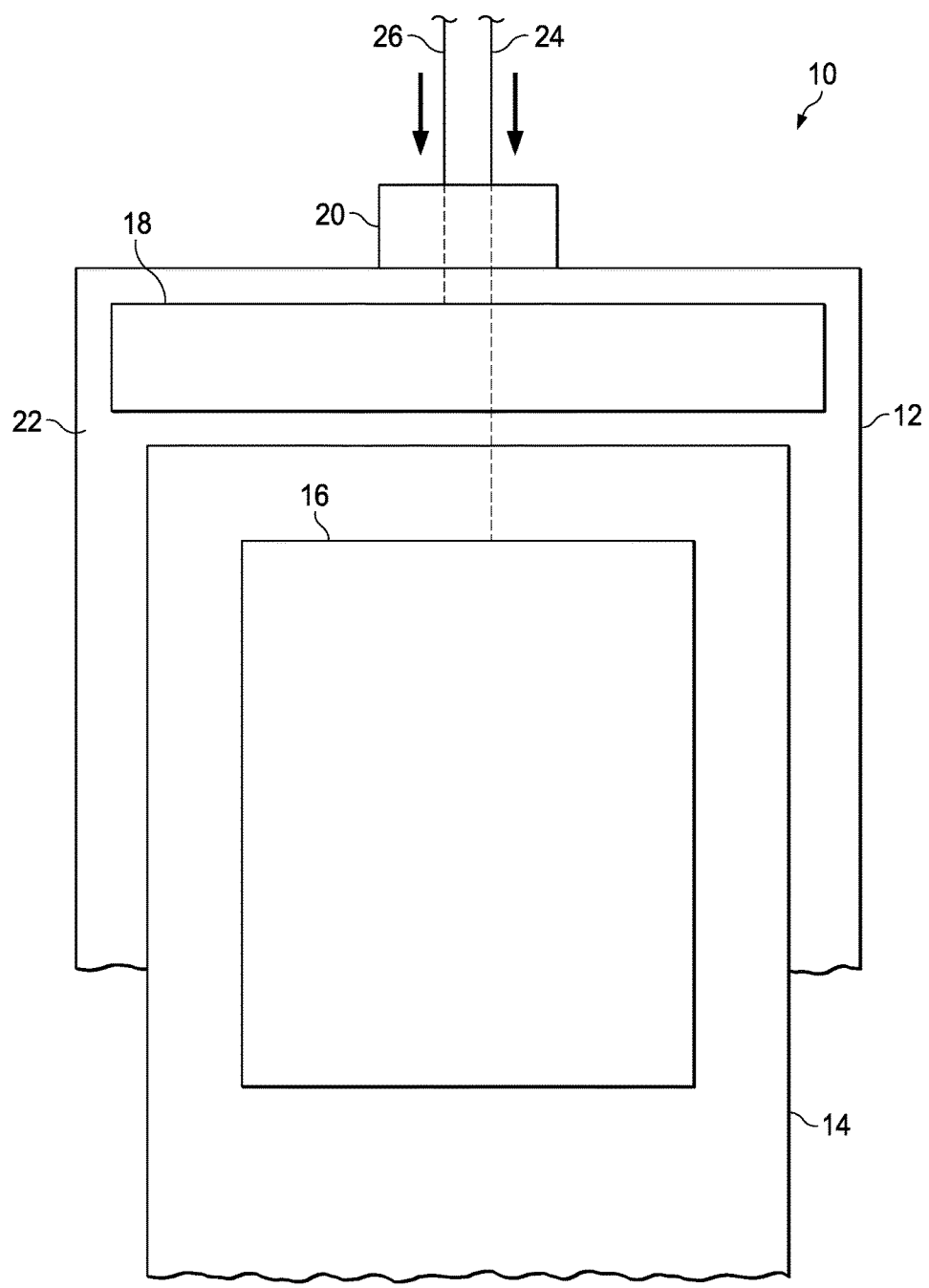
FIG. 1 is a schematic illustration of a syringe-based transfer device according to one embodiment.

Referring now to FIG. 1, a schematic illustration of a portion of a syringe-based transfer device 10 is shown according to an embodiment. Generally, the syringe-based transfer device 10 (also referred to herein as "syringe-based device", "bodily-fluid transfer device," "fluid transfer device," or "transfer device") can be designed or configured to facilitate the withdrawal, procurement, or procuring of bodily-fluid from a patient such that a first portion or amount of the withdrawn fluid is fluidically isolated and diverted away from a second portion or amount of the withdrawn fluid that is to be used as a biological sample, such as for testing for the purpose of medical diagnosis and/or treatment. The transfer device 10 can be configured to transfer a first, predetermined or selected amount of a bodily-fluid to a first collection reservoir and a second amount of bodily-fluid to one or more bodily-fluid collection reservoirs (e.g., sample reservoirs) fluidically isolated from the first collection reservoir.

The transfer device 10 can include a housing 12, an actuator mechanism 14, a first fluid reservoir 16 (also referred to herein as "first reservoir" or "pre-sample reservoir"), and a second fluid reservoir 18 (also referred to herein as "second reservoir" or "sample reservoir"), different from the first fluid reservoir 16. The housing 12 can be any suitable shape, size, or configuration and is described in further detail herein with respect to specific embodiments. As shown in FIG. 1, the housing 12 can include a port 20 that can be at least temporarily physically and fluidically coupled to a medical device defining a pathway for withdrawing and/or conveying the bodily-fluid from the patient to the transfer device 10. For example, the port 20 can be a LUER-LOK or the like configured to be physically and fluidically coupled to a central line, a PICC (peripherally inserted central catheter) line, a needle, a cannula, other lumen-containing devices, or the like. In other embodiments, the port 20 can be monolithically formed with at least a portion of the lumen-containing device.

In example embodiments, the port 20 can include a one-way valve such that fluid flow is unidirectional into the transfer device 10 in the direction shown by the arrows of FIG. 1. The one-way valve can be monolithically formed with the port 20, fixedly coupled with the port 20, or selectively coupled with the port 20. In certain embodiments, the one-way valve can be threadedly coupled with the port 20, attached with a press fit, or can be formed as a one piece, unitary construction with the port 20. The incorporation of such a one-way valve can facilitate a "closed system" as described in more detail herein. During use, the one-way valve can prevent fluid, such as sample blood, from being expelled from the port 20 for the entirety of a blood collection procedure. Such a "closed system" may have advantages over existing systems that both draw and expel fluid, such as blood, through the same port. Drawing and expelling blood through the same port may increase the likelihood that a sample will be contaminated. A "closed system" may also reduce the number of cap entries required to draw blood effectively from, for example, a Central Venous Catheter (CVC) line.

As shown in FIG. 1, the housing 12 can define an inner volume 22 that can be configured to receive a portion of the actuator mechanism 14. More specifically, the actuator mechanism 14 can be at least partially disposed within the inner volume 22 defined by the housing 12 and can be movable between a first configuration and a second configuration relative to the housing 12. The housing 12 can also be configured define at least a portion of the second reservoir 18 as will be described in more detail herein.

In certain embodiments, the first reservoir 16 can be housed within a portion of the actuator mechanism 14 and can be configured to draw any suitable fluid, such as waste blood or a pre-sample, from a patient. The first reservoir 16 can be defined by any suitable structure or combination of structures such as, for example, a pre-sample syringe having a plunger and a threaded distal end that is selectively coupled with a one-way valve. The pre-sample syringe can be used to draw fluid, such as waste blood, into the first reservoir 16, where the pre-sample syringe defining the first reservoir 16 can be selectively removable from the actuator mechanism 14.

There are many circumstances in which it may be advantageous to selectively detach the first reservoir 16 from the transfer device 10. For example, in neonatal applications it may be desirable to return the "waste" blood or pre-sample to the patient after removal of a sample. Providing a selectively removable first reservoir 16 in the form of a selectively detachable pre-sample syringe can allow for this waste or pre-sample to be drawn, an uncontaminated sample to be subsequently drawn, and then the pre-sample is returned to the patient in an autologous transfusion. Any suitable mechanism to remove the pre-sample from the first reservoir 16 is contemplated where, for example, the pre-sample syringe can include a plunger that can be used to expel the fluid. There may not be a need to return the pre-sample to most adults, but there may still be opportunities where accessing or returning the pre-sample is desirable. For example, in patients having certain autoimmune diseases it may be desirable to return even the smallest amount of blood in an autologous transfusion. For both adult and neonatal applications it may be desirable to test or otherwise use the pre-sample instead of simply discarding this fluid with the transfer device 10. For neonatal applications it will be appreciated that the pre-sample syringe or other container can be heparinized or the like to reduce potentially hazardous clotting factors.

The second reservoir 18 can be at least partially defined by a set of walls of the housing 12 that define the inner volume 22. For example, the second reservoir 18 can be a cavity defined by the distal end or plunger of the actuator mechanism 14 and the housing 12, where the plunger and housing 12 can cooperate to form a substantially fluidically sealed chamber. The second reservoir 18 can have a variable volume, where drawing the actuator mechanism 14 proximally can correspondingly increase the volume of the second reservoir 18. A portion of the piston or plunger can form a substantially fluid tight seal with the walls of the housing 12 defining the inner volume 22. In this manner, the housing 12 and the actuator mechanism 14 can collectively form a sealed, air-tight cavity (e.g., a syringe) such that the actuator mechanism 14 (or at least a portion of the actuator mechanism 14) can be configured to introduce or otherwise facilitate the development of a vacuum within the inner volume 22.

The actuator mechanism 14 can have any suitable shape, size, or configuration and can include any suitable number or type of components. For example, in some embodiments, the shape and size of at least a portion of the actuator mechanism 14, such as the outer portion, can substantially correspond to the shape and size of the walls of the housing 12 defining the inner volume 22. As described above, at least a portion of the actuator mechanism 14 can be movably disposed within the inner volume 22 of the housing 12. For example, in some embodiments, a distal end portion of the actuator mechanism 14 can be disposed within the inner volume 22 of the housing 12 and a proximal end portion of the actuator mechanism 14 can be disposed substantially outside the housing 12. In such embodiments, a user can engage the proximal end portion of the actuator mechanism 14 to move the portion of the actuator mechanism 14 disposed within the inner volume 22 proximally to draw fluid into the second reservoir 18.

In some embodiments, the actuator mechanism 14 can include a first member and a second member. The first member and the second member can be collectively moved within the inner volume 22 of the housing 12. In addition, the first member and the second member can be configured to move independently within the housing 12. Similarly stated, the first member can be moved relative to the second member and/or the second member can be moved relative the first member, as further described herein with respect to specific embodiments. In some embodiments, the first member and/or the second member can form a piston or plunger configured to move within the inner volume 22. In one embodiment the first member is a first pre-sample syringe and the second member cooperates with the housing 12 to function as a second syringe. Such a system can be described as a "dual syringe" system.

The first reservoir 16 can be any suitable reservoir for containing the bodily-fluid. For example, in some embodiments, the first reservoir 16 can be defined by an internal syringe, such as a pre-sample syringe, comprising the first member of the actuator mechanism 14. In some embodiments, the first reservoir 16 can be a pre-sample reservoir. The first reservoir 16 can be selectively placed in fluid communication with the housing 12 or the actuator mechanism 14. The first reservoir 16 and/or the first member (e.g., a pre-sample syringe) can be selectively detachable from the actuator mechanism 14.

The first reservoir 16 can be sized to receive and contain the first, predetermined amount of the bodily-fluid. During use, the first member (e.g., a pre-sample syringe) of the actuator mechanism can define a first fluid flow path 24 to fluidically couple the port 20 of the housing 12 to the first reservoir 16. In some embodiments, a portion of the actuator mechanism 14, such as the plunger of the pre-sample syringe, can be urged proximally and can introduce a vacuum that facilitates the flow of the bodily-fluid through the first fluid flow path 24 and into the first reservoir 16. The first reservoir 16 can be designed and sized to retain the first amount of the bodily-fluid such that the first amount is fluidically isolated from a second amount of the bodily-fluid (different than the first amount of bodily-fluid) that is subsequently withdrawn from the patient.

In certain embodiments, the actuator mechanism 14 and the first reservoir 16 can be sized and configured with a pre-set amount of pre-sample that will be withdrawn during a collection procedure. Such a pre-set embodiment may be desirable when a consistent amount of "waste" or pre-sample is withdrawn during most or all blood collection procedures. For example, the actuator mechanism 14 and first reservoir 16 can be size to receive about 3 ml of fluid, about 5 ml of fluid, or any other suitable amount of fluid. In alternate embodiments, it may be desirable to provide a user-selectable volume of pre-sample or "waste" fluid. For example, in neonatal applications it may be desirable to withdraw 1 ml or less of fluid, whereas for a larger adult it may be desirable to withdraw from about 3 ml to about 5 ml of waste blood. Examples of such embodiments will be described in more detail herein where, for example, a clinician can establish a desired pre-sample volume before a procedure and/or can adjust the volume of the sample taken during the collection procedure.

The second reservoir 18 can be any suitable reservoir and can be configured to receive and contain the second amount of the bodily-fluid. In some embodiments, the second reservoir 18 can be defined by a portion of the walls of the housing 12 defining the inner volume 22 and a portion of the actuator mechanism 14. In this manner, when the actuator mechanism 14 is in the second configuration, a portion of the actuator mechanism 14 and a portion of the housing 12 can define a second fluid flow path 26 to fluidically couple the port 20 to the second reservoir 18. It will be appreciated the first and second fluid flow paths 24, 26 can pass initially through the same lumen of the port 20. In some embodiments, the movement of the actuator mechanism 14 proximally can be such that a second vacuum force facilitates the flow of the bodily-fluid through the second fluid flow path 26 and into the second reservoir 18. The second amount of bodily-fluid can be an amount withdrawn from the patient subsequent to withdrawal of the first amount. In some embodiments, the second reservoir 18 is configured to contain the second amount of the bodily-fluid such that the second amount is fluidically isolated from the first amount of the bodily-fluid.

As described above, the transfer device 10 can be used to transfer a bodily-fluid from a patient to the first reservoir 16 and/or second reservoir 18 included in the transfer device 10. More specifically, the flow of the first amount of bodily-fluid transferred to the first reservoir 16 can be such that undesirable microbes, pathogens, contaminants, saline used to flush a central line, heparin used to flush a central line, or the like, become entrained in the flow and are transferred to the first reservoir 16. The first reservoir 16 can fluidically isolate the first amount such that when the subsequent second amount is withdrawn into the second reservoir 18, the second amount is substantially free from such contaminants.

In some embodiments, the transfer device 10 can be configured such that the first amount of bodily-fluid must be conveyed to the first reservoir 16 before the transfer device 10 will permit the flow of the second amount of bodily-fluid conveyed through the second flow path 26 to the second reservoir 18. In such embodiments, the transfer device 10 can be characterized as requiring compliance by a health care practitioner regarding the collection of the first, predetermined amount (e.g., a pre-sample) prior to collection of the second amount (e.g., a sample) of bodily-fluid. Similarly stated, the transfer device 10 can be configured to prevent a health care practitioner from collecting the second amount, or the sample, of bodily-fluid into the second reservoir 18 without first diverting the first amount, or pre-sample, of bodily-fluid into the first reservoir 16. In this manner, the health care practitioner is prevented from including (whether intentionally or unintentionally) the first amount of bodily-fluid, which is more likely to contain microbes and/or other undesirable contaminants, in the bodily-fluid sample to be used for analysis. In other embodiments, the fluid transfer device 10 need not include a forced-compliance feature or component.

In some embodiments, the actuator mechanism 14 can be configured to expel or dispense the bodily fluid retained within the second reservoir 18. It may be desirable, for example, to provide an efficient mechanism in which to transfer the sample blood from the second reservoir 18 into a collection receptacle or the like for testing. In one embodiment, the first fluid reservoir 16 can maintain the first amount of bodily-fluid in fluid isolation and the second fluid reservoir 18 can be maintained in fluid communication with the port 20. When the actuator mechanism 14 is moved distally the transfer device 10 can transfer a portion of the second amount of the bodily-fluid from the second reservoir 18 to any suitable container (e.g., a vile, a test tube, a petri dish, a culture medium, a test apparatus, or the like) such that the portion of the second amount of bodily-fluid can be tested.

In alternate embodiments, it may be advantageous to close or seal the port 20 such that the sample from the second reservoir 18 cannot be expelled through the port 20 or the distal end of the transfer device 10. Such embodiments can represent a "closed system" that can reduce the likelihood that a sample is contaminated and/or the number of cap entries that may be required during a procedure. In one embodiment of such a "closed system", the port 20 can include a one-way valve that permits the inflow of fluid during the collection procedure, but prevents fluid, including the sample, from being expelled through the port 20. In order to access the sample within the second reservoir 18 a portion of the actuator mechanism 14, such as the first member (including first reservoir 16 and/or the pre-sample syringe), can be selectively removed from the transfer device 10 by threadedly disengaging the pre-sample syringe from a one-way valve coupled with the actuator mechanism 14. Subsequently, a fluid transfer adapter (e.g., a BD VACUTAINER LUER-LOK Access Device having a pre-attached multiple sample adapter) can be threadedly engaged with the one-way valve associated with the actuator mechanism 14. The fluid transfer adapter can be positioned at least partially within the inner volume 22 defined by the housing 12. After the fluid transfer adapter is attached to the one-way valve of the actuator mechanism 14 a fluid collection receptacle can be engaged with the fluid transfer adapter to receive the contents of the second reservoir 18. To actively fill the container with the sample from the second reservoir 18 the clinician can advance the actuator mechanism 14 distally, which can result in the fluid from the second reservoir 18 flowing through the proximal end of the second reservoir and into the fluid collection receptacle. In such a system the sample from the second reservoir 18 is expelled from the proximal end rather than the distal end of the of the transfer device 10.

In alternate embodiments, it may be beneficial to incorporate a fluid transfer adapter as described above directly into the transfer device 10 such that the fluid transfer adapter does not need to be manually attached by a clinician. Such a fluid transfer adapter can be monolithically formed in a unitary, one piece construction with the actuator mechanism 14. Such embodiments can provide a "closed system", where the sample fluid is expelled from the proximal end of the transfer device 10, in an efficient manner that reduces the likelihood of accidental needlesticks, the number of cap entries associated with CVC lines, and a reduced likelihood of contamination.

FIGS. 2-13 illustrate a syringe-based transfer device 110 according to several embodiments. The syringe-based transfer device 110 (also referred to herein as "bodily-fluid transfer device," "fluid transfer device," or "transfer device") includes a housing 112 and an actuator mechanism 114. The transfer device 110 can be configured to include or define a first fluid reservoir 116 (also referred to herein as "first reservoir" or "pre-sample reservoir") and a second fluid reservoir 118 (also referred to herein as "second reservoir" or "sample reservoir"). The transfer device 110 can be any suitable shape, size, or configuration. For example, while shown in FIGS. 2 and 3 as being substantially cylindrical, the transfer device 110 can be square, rectangular, polygonal, and/or any other non-cylindrical shape.

Figure 2:
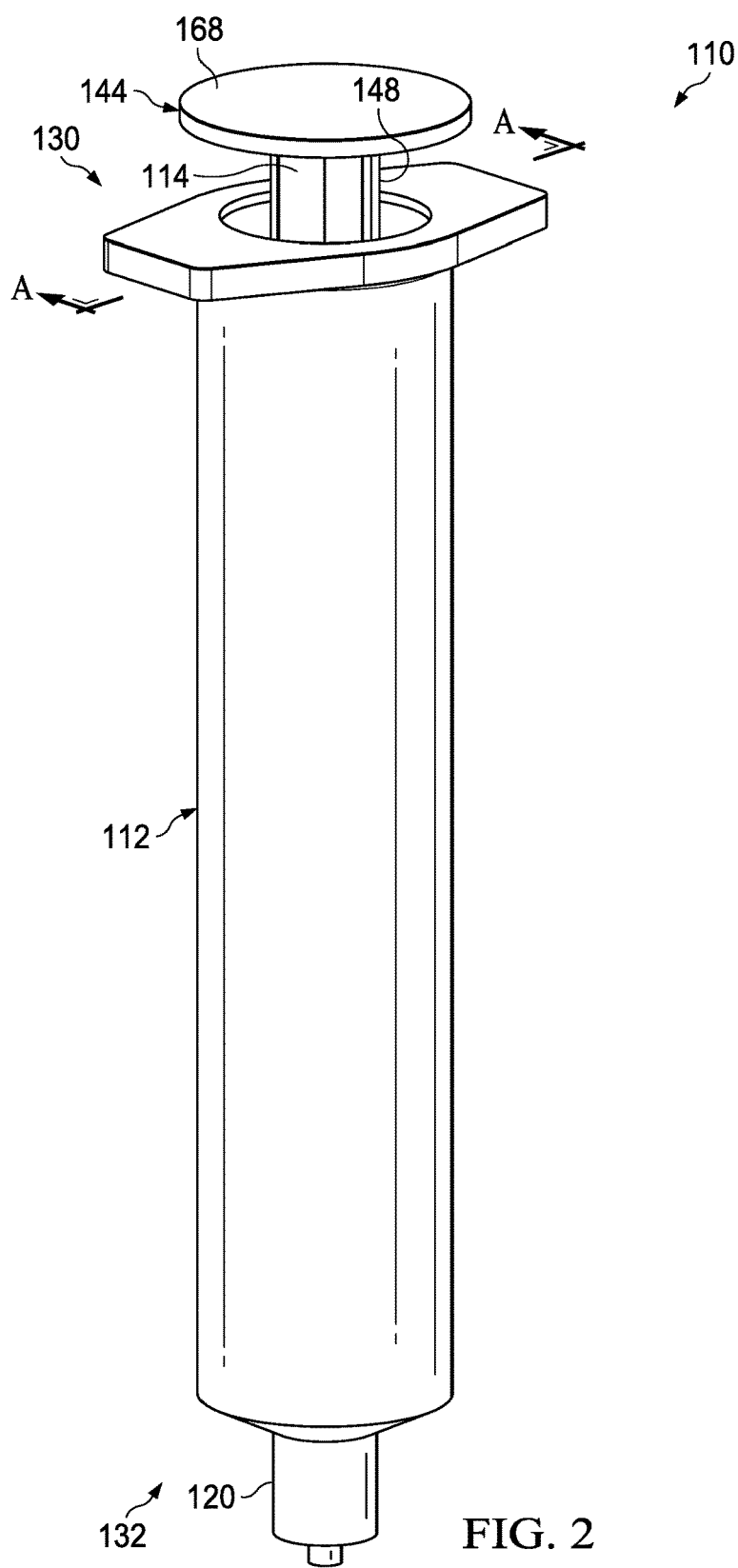
FIG. 2 depicts a perspective view of a dual syringe blood collection system according to one embodiment.
Figure 3:
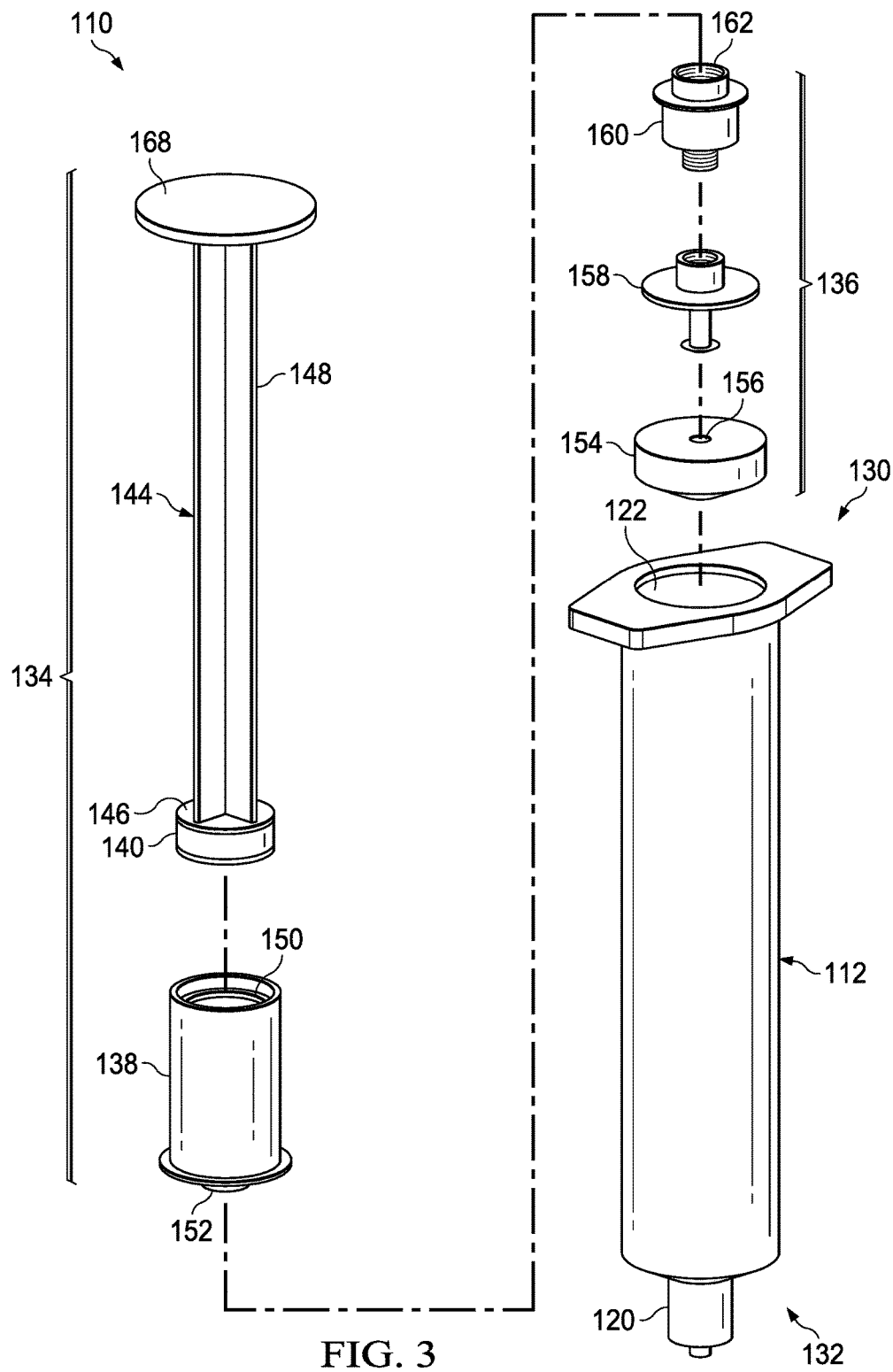
FIG. 3 depicts an exploded view of the dual syringe blood collection system shown in FIG. 2.
Figure 4:
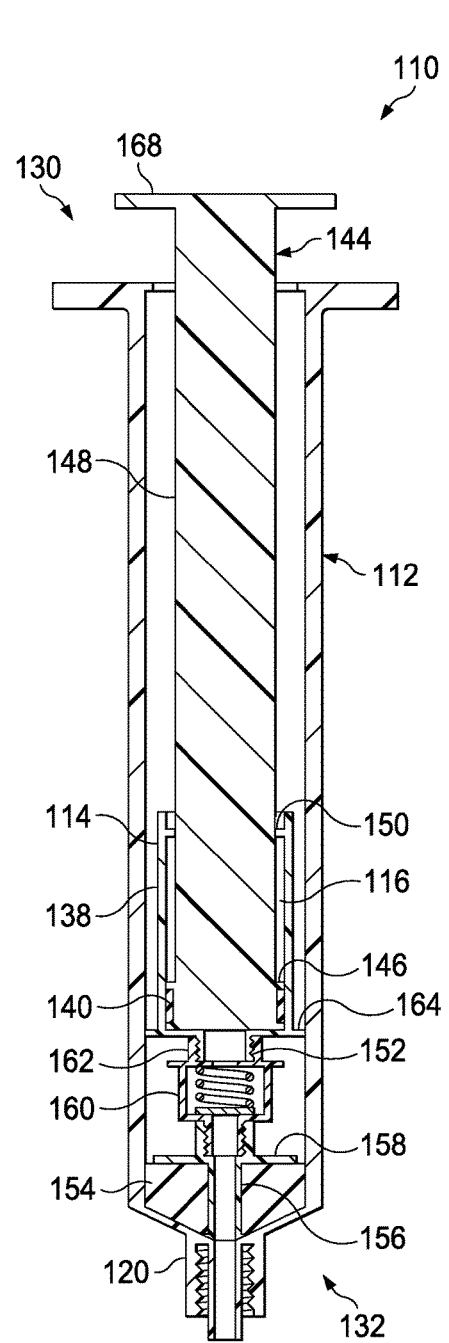
FIG. 4 depicts a cross-sectional view of the dual syringe blood collection system of FIG. 2 taken along reference line A-A and shown in a pre-use configuration.

As shown in FIGS. 2 and 3, the housing 112 can include a proximal end portion 130 and a distal end portion 132 and can define an inner volume 122 therebetween. In some embodiments, the housing 112 can be substantially similar to a syringe body. The proximal end portion 130 of the housing 112 can be substantially open and can be configured to receive at least a portion of the actuator mechanism 114 such that at least the portion of the actuator mechanism 114 can be movably disposed within the inner volume 122. Furthermore, the inner volume 122 can be configured to define the second fluid reservoir 118, as further described herein. The distal end portion 132 of the housing 112 can include a port 120. In some embodiments, the port 120 can be monolithically formed with the housing 112 (e.g., as shown in FIGS. 2 and 3). In other embodiments, the port 120 can be coupled to the distal end portion 132 in any suitable manner such as, for example, via a friction fit, a threaded coupling, a mechanical fastener, an adhesive, any number of mating recesses, and/or any combination thereof.

The port 120 can be any suitable shape, size, or configuration. For example, in some embodiments, at least a portion of the port 120 can form a lock mechanism configured to be physically and fluidically coupled to a Central Venous Catheter (CVC) line, a PICC lines, a needle, a cannula, or other lumen-containing device. For example, in some embodiments, the port 120 can be a LUER-LOK or similar locking mechanism that can be configured to physically and fluidically couple to a CVC line (not shown). In other embodiments, the port 120 can be monolithically formed in a unitary, one piece construction with at least a portion of the lumen-containing device. In this manner, the port 120 can be placed in fluid communication with a lumen defined by the lumen-defining device and to receive the bodily-fluid from a patient when the lumen-defining device is disposed within the patient. In some embodiments, where relatively large syringes are used, it may be advantageous to provide a longer port or an extension from the port such that pressure induced by the larger syringe does not collapse a patient's line. The port and/or extension can be from about 0.5 inches to about 2 inches, from about 1 inch to about 1.5 inches, or any suitable length.

The actuator mechanism 114 can be disposed within the inner volume 122 and can be movable, translatable, or transitionable between a first configuration (e.g., a distal position relative to the housing 112) and a second configuration (e.g., a proximal position relative to the housing 112). The movement of the actuator mechanism 114 relative to the housing 112 can move the transfer device 110 between a number of different configurations and positions, as further described herein. The actuator mechanism 114 can include a first member 134 and a second member 136. The first member 134 of the actuator mechanism 114 can include a plunger 144 and a pre-sample syringe body 138 that can define an inner volume 142 therebetween. At least a portion of the inner volume 142 can be configured to define the first fluid reservoir 116, as further described herein. The plunger 144 can include a plunger seal 140 that can fluidically seal the first fluid reservoir 116.

The pre-sample syringe body 138 can include an open proximal end such that the plunger 144 can be movably disposed within the inner volume 142. The plunger 144 can include one or a plurality of protrusions 146 or projections that can extend radially or laterally outward from a plunger shaft 148 such that the one or a plurality of protrusions 146 can be configured to selectively engage a stop 150 positioned on the inner surface of the pre-sample syringe body 138. The one or a plurality of protrusions 146 can be fixedly coupled or coupleable with the stop 150, where the protrusions 146 can engage the stop 150 in a snap fit, such that the plunger 144 and the pre-sample syringe body 138 are locked such that relative movement between the components cannot occur. It will be appreciated that any suitable mechanism of engagement is contemplated, including reversing the illustrated components, where such engagement can result in a fixed or selectively detachable coupling.

The distal end portion of the first member 134 can include an attachment element 152, such as a LUER-LOK or similar locking or coupling mechanism, that can be configured to selectively physically and fluidically couple the first member 134 with the second member 136. The attachment element 152 can be threadedly engaged with the second member such that rotation of the first member 134 (e.g., 90 degrees in a clockwise direction) will disengage the first member 134 from the 136. The attachment element 152 can include a port which can, for example, be similar in construction and operation to port 120 described herein. It will be appreciated that the attachment element 152 can be selectively attached and decoupled from the second member 136 in any suitable manner such as, for example, with a threaded engagement, a snap fit, and friction fit, a user-accessible locking mechanism, or the like.

The second member 136 can include a plunger seal 154 that can form a friction fit with the inner surface of the walls defining the inner volume 122 when the actuator mechanism 114 is disposed within the housing 112. Similarly stated, the plunger seal 154 can define a fluidic seal with the inner surface of the walls defining the inner volume 122 such that a portion of the inner volume 122 distal of the plunger seal 154 is fluidically isolated from a portion of the inner volume 122 proximal of the plunger seal 154. The plunger seal 154 can define a channel 156 that that can extend through a distal end and a proximal end of the plunger seal 154. A portion of an inner set of walls defining the channel 156 can accept a valve seat 158. In this manner, a portion of the channel 156 can receive a valve 160 that is in contact with the valve seat 158. The valve 160 can include a threaded proximal end 162 that can selectively engage the attachment element 152 of the first member 134 as described herein.

The valve 160 can be any suitable valve. For example, in some embodiments, the valve 160 can be a one-way check valve to allow a flow of a fluid from a distal end of the valve 160 to a proximal end of the valve 160, but substantially not allow a flow of the fluid from the proximal end to the distal end. The valve 160 can be disposed within the channel 156 and can be in contact with the valve seat 158 such that the valve 160 forms a substantially fluid tight seal with the walls defining the channel 156. In some embodiments, the valve 160 can form a friction fit with walls defining the channel 156. In other embodiments, the valve 160 can form a threaded coupling or the like with at least a portion of the walls. The valve 160 can also include a seal member configured to engage the valve seat 158 to form at least a portion of the fluid tight seal.

As described above, the second member 136 can be movably disposed within the housing 112. More specifically, the second member 251 can be movable between a first position (e.g., a distal position) and a second position (e.g., a proximal position) to create a vacuum or negative pressure to draw a sample into the second fluid reservoir 118. The pre-sample syringe body 138 can include a radial projection 164 that extends in a lateral direction to selectively engage a protrusion 166 of the housing 112. In this manner, the radial projection of the actuator mechanism 114 and the protrusion 166 of the housing 112 can be placed in contact to substantially limit a proximal movement of the second member 136 relative to the housing 112. The relative position of the radial projection 164 and the protrusion 166 can be set such that the second member 136 can be urged proximally to a pre-set fill volume for the second fluid reservoir 118. Additionally or alternatively the radial projection 164 and the protrusion 166 can be positioned and cooperate to prevent the actuator mechanism 114 from being removed proximally from the housing 112.

In use, with reference to FIGS. 4-9, a user can engage the transfer device 110 to couple the port 120 to a proximal end portion of a lumen-defining device (not shown) such as, for example, a CVC line, a PICC line, a butterfly needle, a cannula assembly, a trocar (which is some cases is used to insert a catheter into a patient), or the like. With the port 120 physically coupled to the lumen-defining device, the port 120 can be placed in fluid communication with the lumen defined by the lumen-defining device. The distal end portion of the lumen-defining device can be disposed within a portion of the body of a patient (e.g., a vein). In this manner, the port 120 is placed in fluid communication with the portion of the body.

Figure 5:
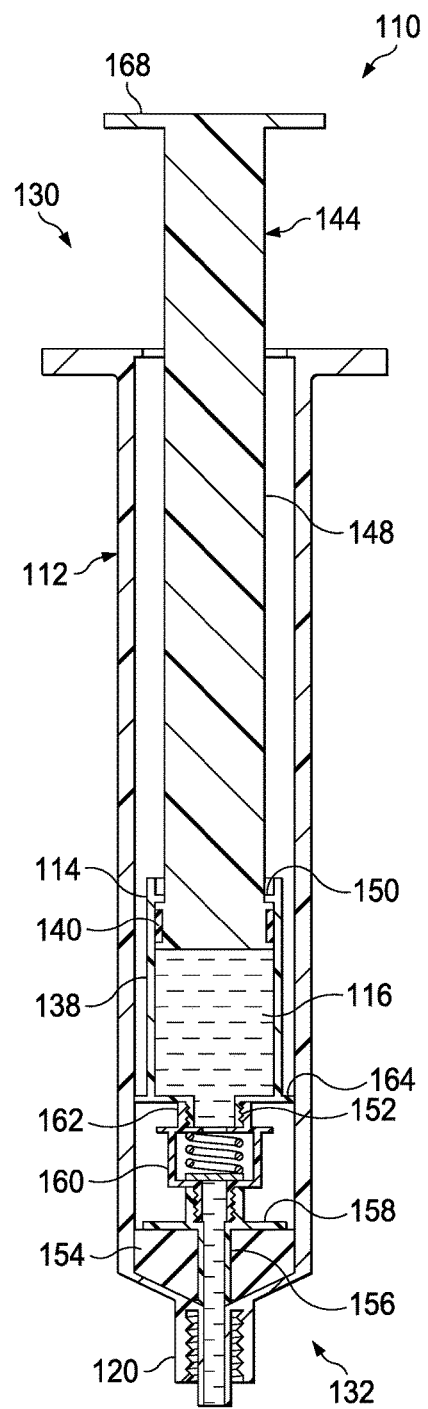
FIG. 5 depicts a cross-sectional view of the dual syringe blood collection system of FIG. 2 shown with a pre-sample drawn into a first reservoir.

With the port 120 coupled to the lumen-defining device, a user (e.g., a phlebotomist, a nurse, a technician, a physician, or the like) can move the transfer device 110 from a first configuration to a second configuration. More specifically, the user can grasp an engagement portion 168 of the plunger 144 to move the plunger seal 140 proximally to create negative pressure or a vacuum within the first fluid reservoir 116. As shown in FIG. 5, the negative pressure in the first fluid reservoir 116 can draw fluid, such as a pre-sample of blood from a patient, into the first fluid reservoir 116. The plunger seal 140 of the plunger 144 can be urged in a proximal direction relative to the pre-sample syringe body 138 until the one or a plurality of protrusions of the plunger shaft 148 is placed into contact with the stop 150 of the pre-sample syringe body 138.

The arrangement of the plunger 144 within the pre-sample syringe body 138 is such that the proximal motion of the plunger 144 increases the volume of the portion of the inner volume 142 that is distal of the plunger seal 140, such that the first fluid reservoir 116 is defined. With the plunger seal 140 forming a fluid tight seal with the inner surface of the walls defining the inner volume 142, the increase of volume can produce a negative pressure within the first fluid reservoir 116.

As shown in FIG. 5, the port 120, the valve 160, the attachment element 152, and the channel 156 can define a fluid flow path that places the first fluid reservoir 116 in fluid communication with the lumen-defining device. Therefore, the first fluid reservoir 116 can correspondingly be placed in fluid communication with the portion of the patient (e.g., the vein). The negative pressure within the first fluid reservoir 116 can be operative in moving the valve 160 from a closed configuration to an open configuration. In this manner, the negative pressure within the within the first fluid reservoir 116 that can be produced by the movement of the plunger seal 140 can introduce a suction force within the portion of the patient. A bodily-fluid can be drawn through the port 120 and the valve 160, through the attachment element 152 of the pre-sample syringe body 138, and into the first fluid reservoir 116. In some embodiments, the bodily-fluid can contain undesirable microbes or contaminant such as, for example, microbes, saline associated with a CVC flush, heparin associated with a CVC flush, or the like.

In some embodiments, the magnitude of the suction force can be modulated by increasing or decreasing the amount of a force applied to the plunger 144. For example, in some embodiments, it can be desirable to limit the amount of suction force introduced to a vein. In such embodiments, the user can reduce the amount of force applied to the engagement portion 168. In this manner, the rate of change (e.g., the increase) in the volume of the first fluid reservoir 116 can be sufficiently slow to allow time for the negative pressure differential between the vein and the fluid reservoir to come to equilibrium before further increasing the volume of the first fluid reservoir 116. Thus, the magnitude of the suction force can be modulated.

While in the second configuration, the transfer device 110 can be configured to transfer a desired amount (e.g., a predetermined amount or a user-selected amount) of bodily-fluid to the first fluid reservoir 116. In some embodiments, the first, predetermined amount can substantially correspond to the size of the first fluid reservoir 116. In other embodiments, the first amount can substantially correspond to an equalization of pressure within the first fluid reservoir 116 and the portion of the patient. Moreover, in such embodiments, the equalization of the pressure can be such that the valve 160 is allowed to return to the closed configuration. Thus, the first fluid reservoir 116 is fluidically isolated from a volume substantially outside the first fluid reservoir 116.

Figure 6:
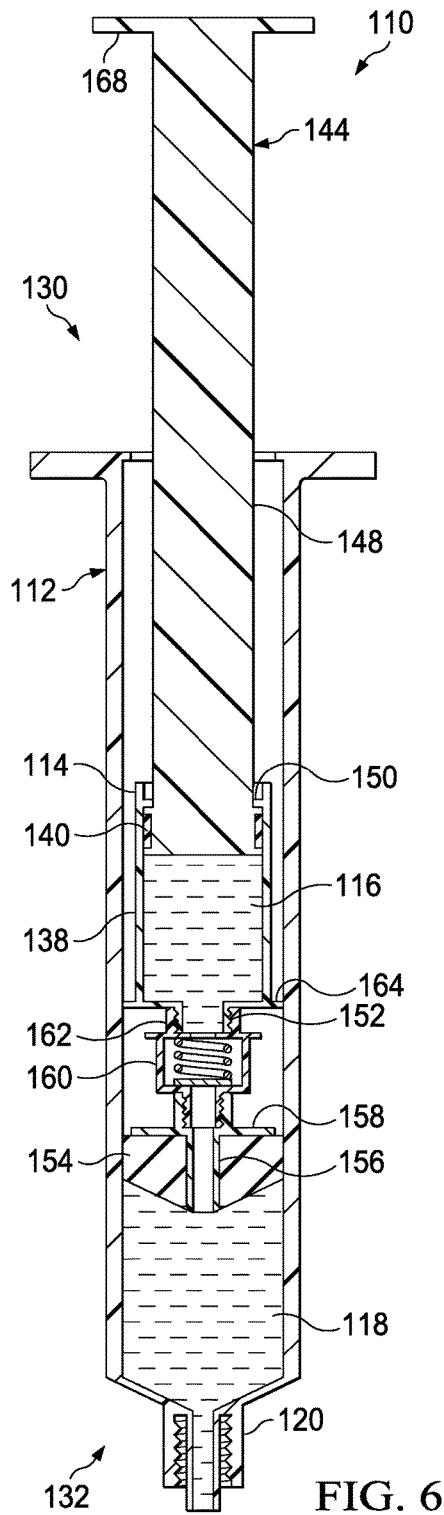
FIG. 6 depicts a cross-sectional view of the dual syringe blood collection system of FIG. 2 shown with a sample drawn into a second reservoir.

With the first amount fluidically isolated, the actuator mechanism 114 can be moved from the second configuration to a third configuration by further moving the plunger 144 in the proximal direction. As shown in FIG. 6, the user can apply a force to the engagement portion 168 of the plunger 144 to move the actuator mechanism 114 relative to the housing 112. With the at least one or a plurality of protrusions 146 of the plunger 144 engaged with the stop 150 of the pre-sample syringe body 138, the further application of force on the engagement portion 168 can be such that the first member 134 and the second member 136 collectively move in the proximal direction relative to the housing 112.

The arrangement of the second member 136 within the inner volume 122 of the housing 112 is such that the proximal motion of the first member 134 and second member 136 increases the volume of the portion of the inner volume 122 that is distal of the plunger seal 154, such that the second fluid reservoir 118 is defined. With the plunger seal 154 forming a fluid tight seal with the inner surface of the walls defining the inner volume 122 and with the valve 160 in the closed configuration, the increase of volume can produce a negative pressure within the second fluid reservoir 118.

As shown in FIG. 6, the port 120 and a portion of the inner volume 122 can define a fluid flow path that places the second fluid reservoir 118 in fluid communication with the lumen-defining device (not shown). As such, the second fluid reservoir 118 can be placed in fluid communication with the portion of the patient (e.g., the vein). The negative pressure within the second fluid reservoir 118 produced by the movement of the plunger seal 154 can introduce a suction force within the portion of the patient. Thus, a bodily-fluid can be drawn through the port 120 and into the second fluid reservoir 118. In addition, the bodily-fluid contained within the second fluid reservoir 118 can be substantially free from microbes, contaminants, saline from a CVC line flush, heparin from a CVC line flush, or the like.

Figure 7:
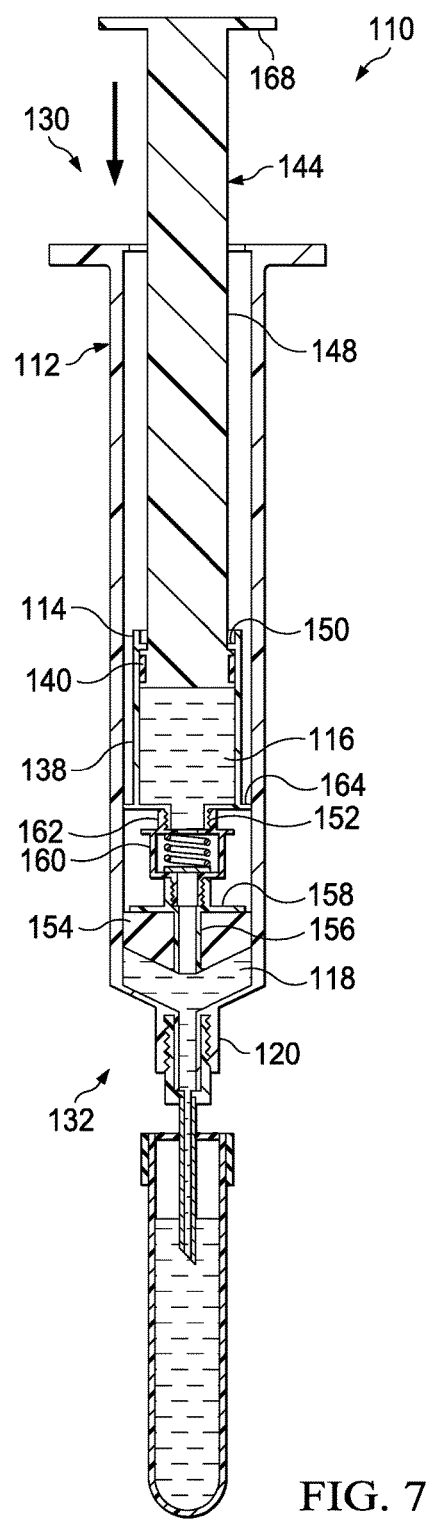
FIG. 7 depicts a cross-sectional view of the dual syringe blood collection system of FIG. 2 shown with the sample being urged from the second reservoir into a fluid receptacle.

As shown in FIG. 7, the transfer device 110 can be moved from the third configuration to a fourth configuration. To expel fluid, the user can apply a force to the engagement portion 168 of the plunger 144 to move the actuator mechanism 114 in the distal direction. With the valve 160 in the closed configuration, and the plunger 144 engaged with the pre-sample syringe body 138, the bodily-fluid contained within the first fluid reservoir 116 is maintained in fluid isolation even as the bodily fluid contained within the second fluid reservoir 118 is expelled. The fluid from the second fluid reservoir 118 can be disposed in a container (e.g., a vile, a test tube, a petri dish, a culture medium, a test apparatus, a cartridge designed for use with an automated, rapid microbial detection system, or the like) such that at least a portion of the second amount of bodily-fluid can be tested. The withdrawn bodily-fluid can be used for any number of testing processes or procedures such as, for example, blood culture testing, real-time diagnostics, and/or PCR-based approaches.

Figure 8:
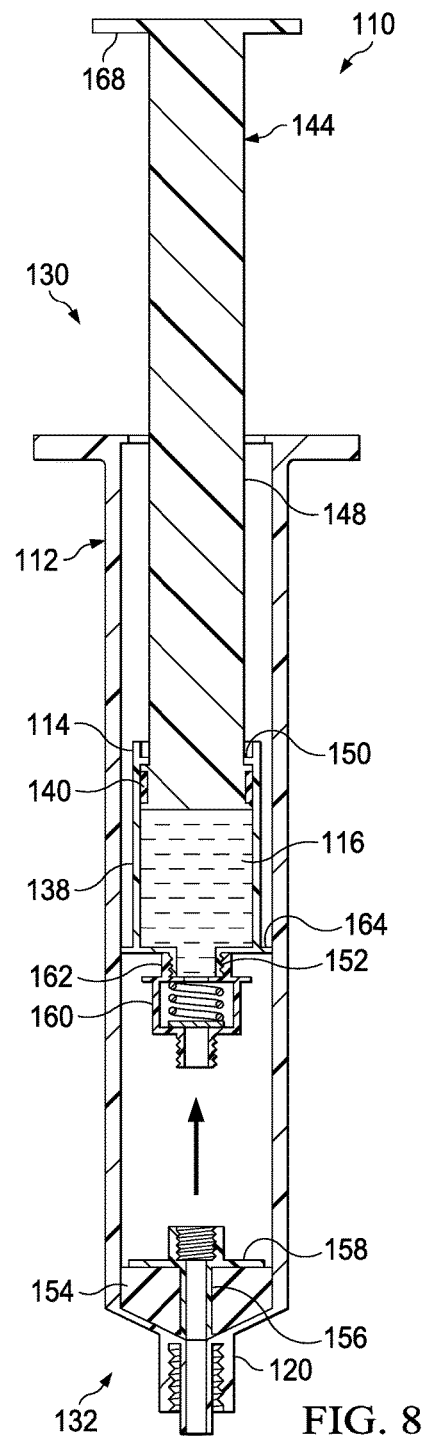
FIG. 8 depicts a cross-sectional view of the dual syringe blood collection system of FIG. 2 shown with the first reservoir being selectively detached from the system.

With reference to FIG. 8, in some embodiments, with the bodily-fluid expelled from the second fluid reservoir 118, the first fluid reservoir 116 can be selectively removed from the housing 112. In some embodiments, the volume of the first fluid reservoir 116 is sufficient to contain the first centiliter or few centiliters of bodily-fluid. In other embodiments, the first fluid reservoir 116 can contain from about 0.1 ml to about 3.0 ml. In still other embodiments, the first fluid reservoir 116 can contain from about 3.0 ml, 4.0 ml, 5.0 ml, 6.0 ml, 7.0 ml, 8.0 ml, 9.0 ml, 10.0 ml, 15.0 ml, 20.0 ml, 25.0 ml, 50 ml, or any volume or fraction of volume therebetween. In one embodiment, the pressure within the first fluid reservoir 116 can be such that the force applied to the plunger 144 does not substantially move the first member 134 relative to the second member 136. In such examples, the force applied to the engagement portion 168 can collectively move the second member 136 and the first member 134 in the distal direction relative to the housing 112 to expel a desired portion of the second amount of bodily-fluid from the lumen-defining device and into the container. In alternate embodiment, the coupling between the plunger 144 and the pre-sample syringe body 138, such as with the mating of the one or a plurality of protrusions 146 and the stop 150, can result in a fixed coupling or temporary fixed coupling such that force applied to the plunger 144 is transferred to the pre-sample syringe body 138 to urge the plunger seal 154 distally to expel the bodily fluid. Such an embodiment may be advantageous as movement of the plunger seal 154 does not require sufficient fluid pressure to be built up in the first fluid reservoir 116 to advance the first member 134.

Figure 9:
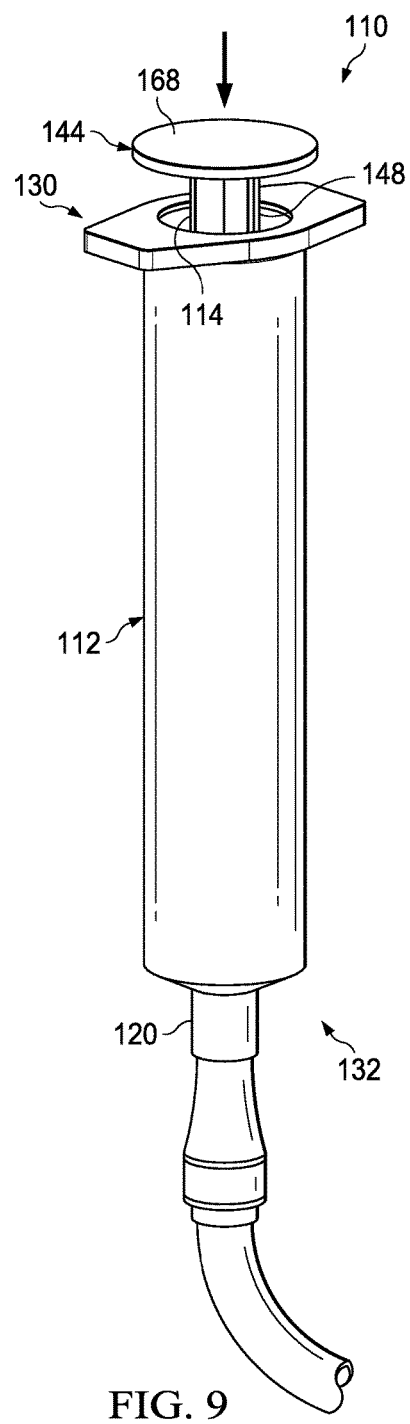
FIG. 9 depicts a perspective view of the selectively detached first reservoir shown in FIG. 8 being used to provide an autologous transfusion to a patient.

As shown in FIG. 9, the transfer device 110 can be transitioned from a fourth configuration to a fifth configuration, where the fifth configuration can be associated with expelling the bodily fluid retained within the first fluid reservoir 116. It may be desirable to access the bodily fluid contained within the first fluid reservoir 116 for a variety of reasons including, for example, neonatal applications where "waste" blood is returned to the patient in an autologous infusion, adult applications where autoimmune disease makes the return of even the smallest amount of blood advantageous, or for separate testing and evaluation procedures. To accomplish this, in one embodiment, after bodily fluid has been expelled from the second fluid reservoir 118, the first member 134 can be detached from the second member 136. The first member 134 can be detached from the second member 136 by unscrewing the attachment element 152 from the threaded proximal end 162 of the valve 160 (e.g., as shown in FIG. 8). Such a configuration can permit the first member 134 containing the first fluid reservoir 116 to be separated and removed from the actuator mechanism 114. Once removed, the attachment element 152 of the first member 134 can be threadedly engaged with or otherwise attached to any suitable lumen-defining device such as a CVC catheter line, a PICC line, or the like (e.g., as shown in FIG. 9). It will be appreciated that all or a portion of the first member 134, such as an inner surface of the pre-sample syringe body 138, can be coated or impregnated with heparin or any other suitable medicament, fluid, or material as desired.

As shown in FIG. 9, after the first member 134 has been attached to a lumen defining device, the plunger 144 can be rotated or otherwise made to disengage the coupling between the one or a plurality of protrusions 146 and the stop 150. It will be appreciated that any suitable engagement between the plunger 144 and the pre-sample syringe body 138 is contemplated that permits initial proximal movement of the plunger 144, a locked position for distal movement of the actuator mechanism 114 to expel fluid from the second fluid reservoir 118, and permits the plunger 144 to be decoupled from the pre-sample syringe body 138 such that the plunger 144 can move distally relative to the pre-sample syringe body 138. After decoupling the plunger 144 and the pre-sample syringe body 138, such as by disconnecting the one or a plurality of protrusions 146 from the stop 150, the plunger 144 can be advance to expel the fluid contained in the first fluid reservoir 116. Fluid passing out of the first fluid reservoir 116 can pass through the attachment element 152, which can have a port configuration similar to port 120, and into the lumen defining device. In this manner, an autologous transfusion can be facilitated that safely and effectively returns all available blood or fluid to a patient. It will be appreciated that the first member 134 can also be attached to a sample vial, collection vial, testing device, or the like, as well.

As illustrated in FIGS. 10 and 11, it may be desirable to provide a clinician with the ability to pre-set or control an amount of bodily-fluid transferred to the first fluid reservoir 116. With the transfer device coupled to a lumen-defining device, the user can grasp an engagement portion 168 of the plunger 144 to move the plunger seal 140 proximally to create negative pressure or a vacuum within the first fluid reservoir 116. The plunger seal 140 of the plunger 144 can be urged in a proximal direction relative to the pre-sample syringe body 138 to draw fluid into the first fluid reservoir 116. In the illustrated embodiment, the plunger shaft 148 can define a cylindrical channel 190, where the cylindrical channel 190 can have an axis substantially perpendicular to the axis of motion for the plunger 144. The cylindrical channel 190 can house a spring 192 and a pin 194, where the spring 192 can bias the pin 194 outwardly. The pre-sample syringe body 138 can define a first aperture 196, a second aperture 197, and a third aperture 198, where the apertures can be sized to accept the pin 194. The apertures 196, 197, 198 can be spaced apart and marked such that each of the apertures corresponds to a different volume of fluid collected in the first fluid reservoir 116. Each of the apertures 196, 197, 198 can be marked with an associated volume such as, for example, 1 ml, 3 ml, and 5 ml, respectively.

During use, the clinician may have a target amount of fluid that it is desirable to draw into the first fluid reservoir 116. For example, in certain neonatal situations where it is preferable to take the smallest amount of "waste" volume necessary, a clinician may wish to set the first member 134 such that only 1 ml of fluid is collected. In this example, where the aperture 197 can correspond to 1 ml of fluid, the clinician can draw the plunger 144 proximally until the outwardly biased pin 194 engages the first aperture 196. Once the pin 194 has engaged the first aperture 196 the first member and the second member can be coupled such that they move concomitantly as discussed herein. If the clinician desires a greater volume, such as 3 ml to be drawn, the clinician could depress the pin 194 positioned in the first aperture 196 while pulling proximally on the plunger 144 such that the pin 194 advance proximally and subsequently engages the second aperture 197. This step can be repeated to engage the pin 194 with the third aperture 198 in the same manner. Such a system can be used to draw a variable amount of fluid with a single device, where the clinician has control over the amount drawn without requiring multiple different devices. Should the fluid within the first fluid reservoir 116 be desirable for an autologous transfusion the pin 194 can be depressed while pushing distally on the plunger 144 to expel the fluid. The apertures 196, 197, 198 can have a substantially linear arrangement, as illustrated, or can be rotationally staggered about the pre-sample syringe body 138. In a staggered relationship it may be possible for the clinician to rotate the plunger 144 relative to the pre-sample syringe body 138 to align the desired aperture with the pin on the first engagement.

Figure 12:
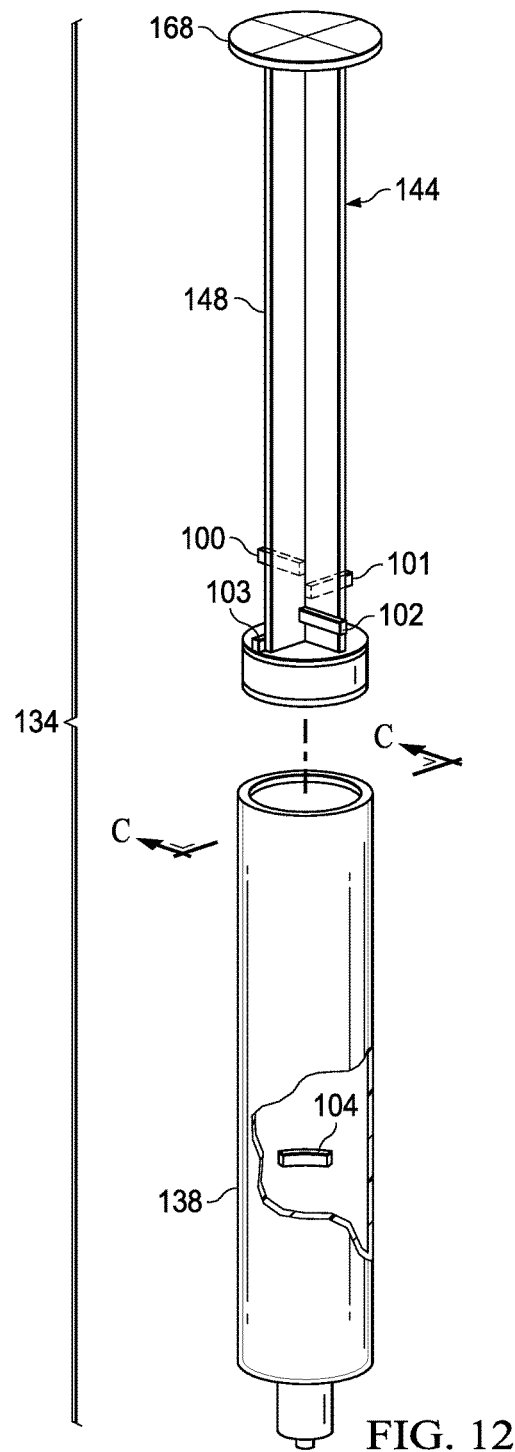
FIG. 12 depicts an exploded and partial cutaway view of pre-sample syringe having a user selectable mechanism for setting a desired pre-sample volume according to one embodiment.
Figure 13:
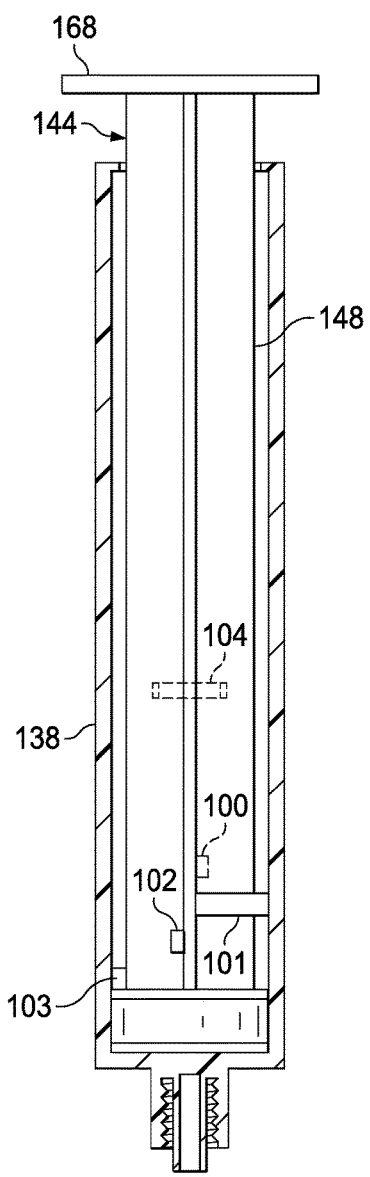
FIG. 13 depicts a cross-sectional view of the pre-sample syringe of FIG. 12, taken along reference line C-C.

FIGS. 12 and 13 illustrate an alternate embodiment of a first member 134 having a user selectable volume. In the illustrated embodiment, the plunger 144 can include a first projection 100, a second projection 101, a third projection 102, and a fourth projection 103, where the projections 100, 101, 102, 103 can be radial extensions or extrusions extending laterally outward from the plunger shaft 148. The projections 100, 101, 102, 103 can each be sized, for example, such that each is a projection making up a 90 degree portion of the plunger shaft 148, which can have a radial configuration. Each of the projections 100, 101, 102, 103, can be spaced apart along a central axis of the plunger shaft 148 to correspond with an associated volume such as, for example, 0.5 ml, 1 ml, 3 ml, and 5 ml, respectively. The first member 134 can be marked (e.g., on the engagement portion 168) with an associated volume. The pre-sample syringe body 138 can include a stop 150, where the stop 104 can be a radially projection extending inward from the pre-sample syringe body 138. The stop 150 can be sized and shaped to selectively engage one of the projections 100, 101, 102, and 103 depending upon the volume of pre-sample desired by the user.

During use, the clinician may have a target amount of fluid that it is desirable to draw into the first fluid reservoir 116. For example, in certain neonatal situations where it is preferable to take the smallest amount of "waste" volume necessary, a clinician may wish to set the first member 134 such that only 0.5 ml of fluid is collected. In this example, where the first projection 100 can correspond to 0.5 ml of fluid, the clinician can rotate the plunger 144 until the first projection 100 is aligned with the stop 104 and draw the plunger 144 proximally. Once the first projection 100 has engaged the stop 150, the first member and the second member can be coupled such that they move concomitantly as discussed herein. If the clinician desires a greater volume, such as 3 ml for example, the clinician can rotate the plunger 144 to align the third projection 102 with the stop 104 and urge the plunger 144 proximally. Such a system can be used to draw a variable amount of fluid with a single device, where the clinician has control over the amount drawn without requiring multiple different devices. Should the fluid within the first fluid reservoir 116 be desirable for an autologous transfusion, or for testing, the plunger 144 can simply be advanced distally to expel the fluid. It will be appreciated that any suitable number of steps having any suitable arrangement and shape are contemplated.

FIG. 14 illustrates a flow chart depicting a Method 1000 for using a fluid transfer device, such as fluid transfer device 110. Method 1000 can include Providing a Fluid Collection System 1002, which can include providing any suitable fluid transfer device. Method 1000 can include Collecting a First Sample of Bodily Fluid in a First Fluid Reservoir 1004, which can include drawing a blood "waste" sample into the first fluid reservoir 116. Method 1000 can include Collecting a Second Sample of Bodily Fluid in a Second Fluid Reservoir 1006, which can include drawing a sample into the second fluid reservoir 118. Method 1000 can include Expelling the Second Sample of Bodily Fluid into a Collection Vial 1008, which can include distally advancing the plunger to expel the sample into a collection vial. Expelling the Second Sample of Bodily Fluid into a Collection Vial 1008 can also include expelling the sample in accordance with "closed systems" described herein (e.g., fluid transfer devices 210 and 310, for example). Method 1000 can include Detaching the First Fluid Reservoir from the Fluid Collection System 1010, which can include physically removing the pre-sample syringe body 138 from the actuator mechanism 114, where the "waste" sample retained within the first fluid reservoir 116 can be remove from the fluid transfer device 110 for testing or any other suitable purpose.

FIG. 15 illustrates a flow chart depicting a Method 1100 for using a fluid transfer device, such as fluid transfer device 110, to deliver an autologous infusion. As described herein, it may be advantageous to transfer the pre-sample or "waste" blood from a sample back to the patient in neonatal applications. Method 1100 can include Providing a Fluid Collection System having a First Syringe and a Second Syringe 1102. Method 1100 can include Collecting a First Sample of Bodily Fluid in the First Syringe 1104. Method 1100 can include Collecting a Second Sample of Bodily Fluid in the Second Syringe 1106. Method 1100 can include Expelling the Second Sample of Bodily Fluid into a Collection Vial 1108, which can include both "open" and "closed" systems in accordance with versions described herein. Method 1100 can include Detaching the First Syringe 1110. Method 1100 can include Delivering an Autologous Infusion Using the First Syringe 1112, which can include delivering the fluid sample retained within the first fluid reservoir 116 to the patient for any suitable purpose.

FIGS. 16-26 illustrate a syringe-based transfer device 210 according to an alternate embodiment. The syringe-based transfer device 210 (also referred to herein as "bodily-fluid transfer device," "fluid transfer device," or "transfer device") includes a housing 212 and an actuator mechanism 214. The transfer device 210 can be configured to include or define a first fluid reservoir 216 (also referred to herein as "first reservoir" or "pre-sample reservoir") and a second fluid reservoir 218 (also referred to herein as "second reservoir" or "sample reservoir"). The transfer device 210 can be any suitable shape, size, or configuration. For example, while shown in FIGS. 16 and 17 as being substantially cylindrical, the transfer device 210 can be square, rectangular, polygonal, and/or any other non-cylindrical shape. As will be described in more detail herein, the syringe-based transfer device 210 can include a selectively attachable fluid transfer adapter 270.

Figure 16:
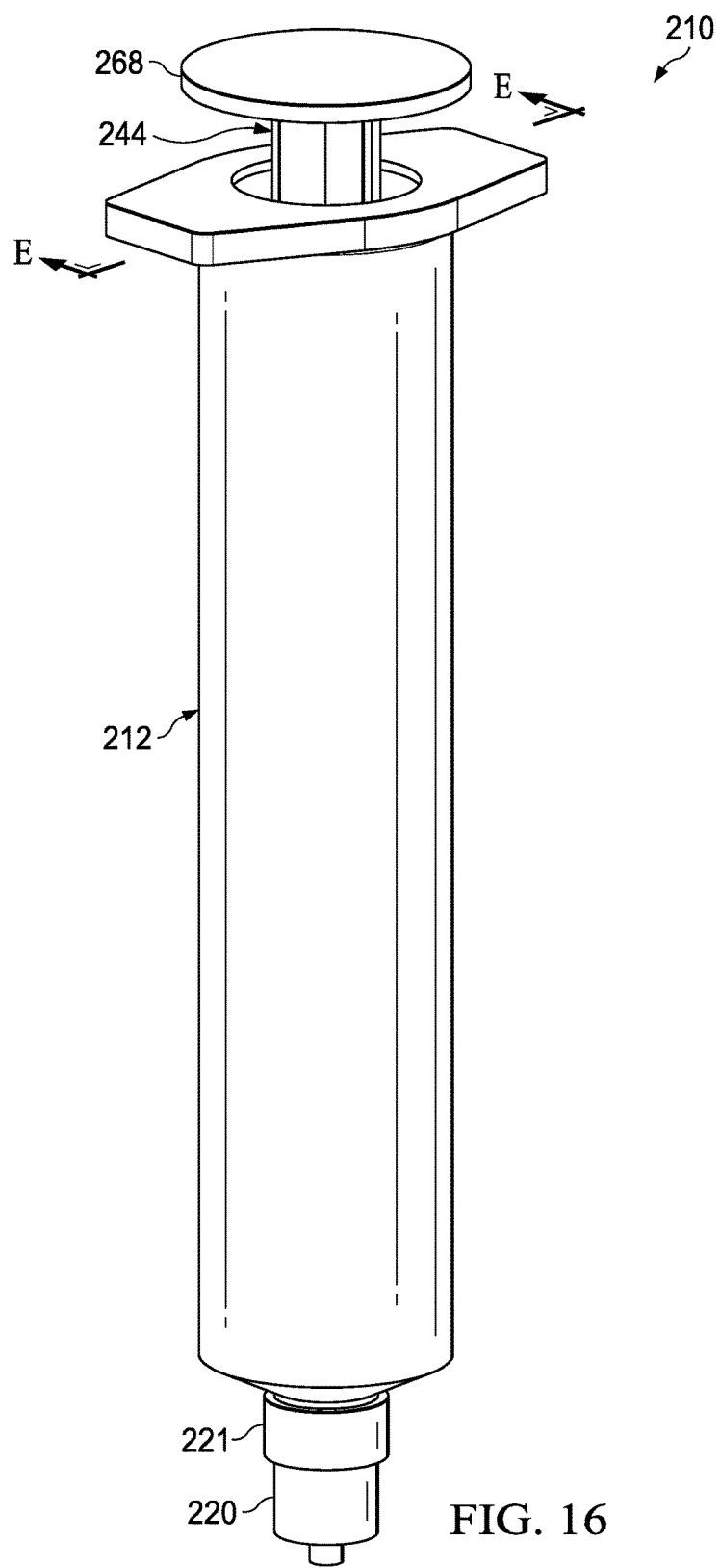
FIG. 16 depicts a perspective view of a dual syringe blood collection system in accordance with a "closed system" according to one embodiment.
Figure 19:
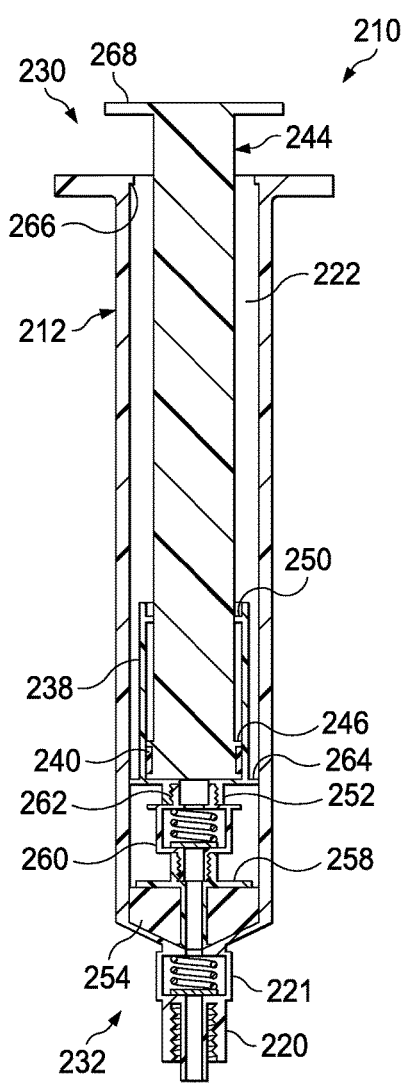
FIG. 19 depicts a cross-sectional view of the dual syringe blood collection system of FIG. 16, taken along reference line E-E and shown in a pre-use configuration.

As shown in FIGS. 16 and 17, the housing 212 can include a proximal end portion 230 and a distal end portion 232 and can define an inner volume 222 therebetween. In some embodiments, the housing 212 can be substantially similar to a syringe body. The proximal end portion 230 of the housing 212 can be substantially open and can be configured to receive at least a portion of the actuator mechanism 214 such that at least the portion of the actuator mechanism 214 can be movably disposed within the inner volume 222. Furthermore, the inner volume 222 can be configured to define the second fluid reservoir 218, as further described herein. The distal end portion 232 of the housing 212 can include a port 220.

In some embodiments, the port 220 can be monolithically formed with the housing 212 (e.g., as shown in FIGS. 16 and 17). The port 220 can include a distal valve 221, which can be a one-way valve, such that fluid can be drawn proximally into the transfer device 210, but not expelled distally outward. The port 220 and/or distal valve 221 can be coupled to the distal end portion 232, can be monolithically formed as a unitary, one piece construction, or can be selectively detachable such as with a threaded coupling. The port 220 and distal valve 221 can alternatively be coupled with the housing 212 in any suitable manner such as, for example, via a friction fit, a threaded coupling, a mechanical fastener, an adhesive, any number of mating recesses, and/or any combination thereof.

The port 220 and distal valve 221 can have any suitable shape, size, or configuration. For example, in some embodiments, at least a portion of the port 220 can form a lock mechanism configured to be physically and fluidically coupled to a Central Venous Catheter (CVC) line, a PICC line, a needle, a cannula, or other lumen-containing device. For example, in some embodiments, the port 220 can be a LUER-LOK or similar locking mechanism that can be configured to physically and fluidically couple to a CVC line (not shown). In other embodiments, the port 220 and/or distal valve 221 can be monolithically formed in a unitary, one piece construction with at least a portion of the lumen-containing device. In this manner, the port 220 and/or distal valve 221 can be placed in fluid communication with a lumen defined by the lumen-defining device and to receive the bodily-fluid from a patient when the lumen-defining device is disposed within the patient.

The actuator mechanism 214 can be disposed within the inner volume 222 and can be movable between a first position (e.g., a distal position relative to the housing 212) and a second position (e.g., a proximal position relative to the housing 212). The movement of the actuator mechanism 214 relative to the housing 212 can move the transfer device 210 between a number of different configurations and positions, as further described herein. The actuator mechanism 214 can include a first member 234 and a second member 236. The first member 234 of the actuator mechanism 214 can include a plunger 244 and a pre-sample syringe body 238 that can define an inner volume 242 therebetween. At least a portion of the inner volume 242 can be configured to define the first fluid reservoir 216, as further described herein. The plunger 244 can include a plunger seal 240 that can fluidically seal the first fluid reservoir 216.

The pre-sample syringe body 238 can include an open proximal end such that the plunger 244 can be movably disposed within the inner volume 242. The plunger 244 can include one or a plurality of protrusions 246 that can extend radially or laterally outward from a plunger shaft 248 such that the one or a plurality of protrusions 246 can be configured to selectively engage a stop 250 positioned on the inner surface of the pre-sample syringe body 238. The one or a plurality of protrusions 246 can be fixedly coupled with the stop 250, where the protrusions 246 can engage the stop 250 in a snap fit, such that the plunger 244 and the pre-sample syringe body 238 are locked such that relative movement between the components cannot occur. It will be appreciated that any suitable mechanism of engagement is contemplated, including reversing the illustrated components, where such engagement can result in a fixed or selectively detachable coupling.

The distal end portion of the first member 234 can include an attachment element 252, such as a LUER-LOK or similar locking or coupling mechanism, that can be configured to selectively physically and fluidically couple the first member 234 with the second member 236. The attachment element 252 can be threadedly engaged with the second member 236 such that rotation of the first member 234 (e.g., 90 degrees in a clockwise direction) will disengage the first member 234 from the second member 236. The attachment element 252 can include a port which can, for example, be similar in construction and operation to port 220 described herein. It will be appreciated that the attachment element 252 can be selectively attached and decoupled from the second member 236 in any suitable manner such as, for example, with a threaded engagement, a snap fit, and friction fit, a user-accessible locking mechanism, or the like.

The second member 236 can include a plunger seal 254 that can form a friction fit with the inner surface of the walls defining the inner volume 222 when the actuator mechanism 214 is disposed within the housing 212. Similarly stated, the plunger seal 254 can define a fluidic seal with the inner surface of the walls defining the inner volume 222 such that a portion of the inner volume 222 distal of the plunger seal 254 is fluidically isolated from a portion of the inner volume 222 proximal of the plunger seal 254. The plunger seal 254 can define a channel 256 that that can extend through a distal end and a proximal end of the plunger seal 254. A portion of an inner set of walls defining the channel 256 can accept a valve seat 258. In this manner, a portion of the channel 256 can receive a valve 260 that is in contact with the valve seat 258. The valve 260 can include a threaded proximal end 262 that can selectively engage the attachment element 252 of the first member 234 as described herein.

The valve 260 can be any suitable valve. For example, in some embodiments, the valve 260 can be a one-way check valve to allow a flow of a fluid from a distal end of the valve 260 to a proximal end of the valve 260, but substantially not allow a flow of the fluid from the proximal end to the distal end. In one embodiment, the valve 260 and the distal valve 221 have the same construction and direction of permissible fluid flow. The valve 260 can be disposed within the channel 256 and can be in contact with the valve seat 258 such that the valve 260 forms a substantially fluid tight seal with the walls defining the channel 256. In some embodiments, the valve 260 can form a friction fit with walls defining the channel 256. In other embodiments, the valve 260 can form a threaded coupling or the like with at least a portion of the walls. The valve 260 can also include a seal member configured to engage the valve seat 258 to form at least a portion of the fluid tight seal.

As described above, the second member 236 can be movably disposed within the housing 212. More specifically, the second member 236 can be movable between a first position (e.g., a distal position) and a second position (e.g., a proximal position) to create a vacuum or negative pressure to draw a sample into the second fluid reservoir 218. The pre-sample syringe body 238 can include a radial projection 264 that extends in a lateral direction to selectively engage a protrusion 266 of the housing 212. In this manner, the radial projection of the actuator mechanism 214 and the protrusion 266 of the housing 212 can be placed in contact to substantially limit a proximal movement of the second member 236 relative to the housing 212. The relative position of the radial projection 264 and the protrusion 266 can be set such that the second member 236 can be urged proximally to a pre-set fill volume for the second fluid reservoir 218. Additionally or alternatively the radial projection 264 and the protrusion 266 can be positioned and cooperate to prevent the entire actuator mechanism 214 from being removed proximally from the housing 212, but as described herein it may be desirable to remove at least a portion of the actuator mechanism 214 during the fluid transfer process.

In use, as shown in FIGS. 19-26, a user can engage the transfer device 210 to couple the port 220 and distal valve 221 to a proximal end portion of a lumen-defining device (not shown) such as, for example, a CVC line, a PICC line, a butterfly needle, a cannula assembly, a trocar (which is some cases is used to insert a catheter into a patient), or the like. With the port 220 physically coupled to the lumen-defining device, the port 220 can be placed in fluid communication with the lumen defined by the lumen-defining device. The distal end portion of the lumen-defining device can be disposed within a portion of the body of a patient (e.g., a vein). In this manner, the port 220 is placed in fluid communication with the portion of the body.

Figure 20:
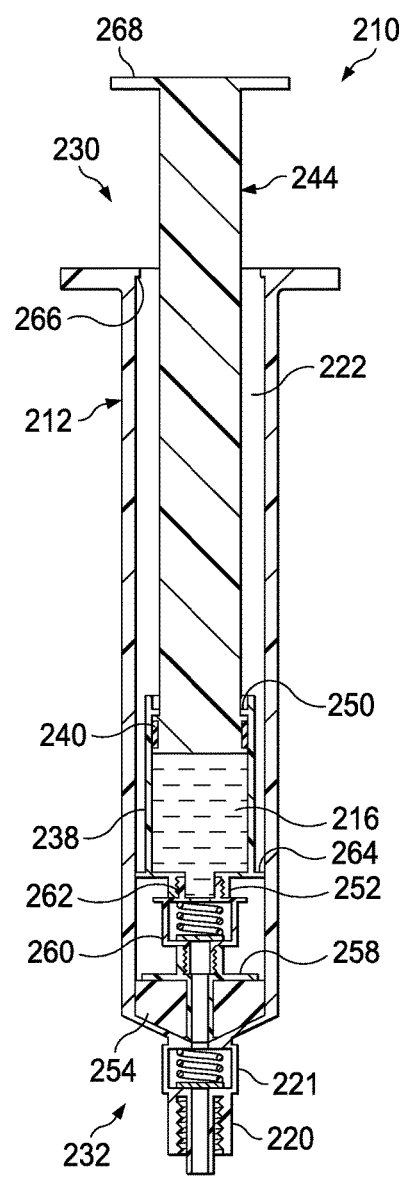
FIG. 20 depicts a cross-sectional view of the dual syringe blood collection system of FIG. 16, shown with a pre-sample drawn into a first reservoir.

With the port 220 coupled to the lumen-defining device, a user (e.g., a phlebotomist, a nurse, a technician, a physician, or the like) can move the transfer device 210 from a first configuration to a second configuration. More specifically, the user can grasp an engagement portion 268 of the plunger 244 to move the plunger seal 240 proximally to create negative pressure or a vacuum within the first fluid reservoir 216. As shown in FIG. 20, the negative pressure in the first fluid reservoir 216 can draw fluid, such as a pre-sample of blood from a patient, through the distal valve 221 and ultimately into the first fluid reservoir 216. The plunger seal 240 of the plunger 244 can be urged in a proximal direction relative to the pre-sample syringe body 238 until the one or a plurality of protrusions of the plunger shaft 248 is placed into contact with the stop 250 of the pre-sample syringe body 238. The distal valve 221 can prevent any of the pre-sample fluid from being expelled distally from the port 220 in the event the plunger 244 is accidentally urged or pushed distally.

The arrangement of the plunger 244 within the pre-sample syringe body 238 can be such that the proximal motion of the plunger 244 increases the volume of the portion of the inner volume 242 that is distal of the plunger seal 240, such that the first fluid reservoir 216 is defined. With the plunger seal 240 forming a fluid tight seal with the inner surface of the walls defining the inner volume 242, the increase of volume can produce a negative pressure within the first fluid reservoir 216.

As shown in FIG. 20, the port 220, the distal valve 221, the valve 260, the attachment element 252, and the channel 256 can define a fluid flow path that places the first fluid reservoir 216 in fluid communication with the lumen-defining device. Therefore, the first fluid reservoir 216 can correspondingly be placed in fluid communication with the portion of the patient (e.g., the vein). The negative pressure within the first fluid reservoir 216 can be operative in moving the valve 260 and the distal valve 221 from a closed configuration to an open configuration. In this manner, the negative pressure within the within the first fluid reservoir 216 that can be produced by the movement of the plunger seal 240 can introduce a suction force within the portion of the patient. A bodily-fluid can be drawn through the port 220, distal valve 221, and the valve 160, through the attachment element 252 of the pre-sample syringe body 238, and into the first fluid reservoir 216. In some embodiments, the bodily-fluid can contain undesirable microbes or contaminant such as, for example, microbes, saline associated with a CVC flush, heparin associated with a CVC flush, or the like.

In some embodiments, the magnitude of the suction force can be modulated by increasing or decreasing the amount of a force applied to the plunger 244. For example, in some embodiments, it can be desirable to limit the amount of suction force introduced to a vein. In such embodiments, the user can reduce the amount of force applied to the engagement portion 268. In this manner, the rate of change (e.g., the increase) in the volume of the first fluid reservoir 216 can be sufficiently slow to allow time for the negative pressure differential between the vein and the fluid reservoir to come to equilibrium before further increasing the volume of the first fluid reservoir 216. Thus, the magnitude of the suction force can be modulated.

While in the second configuration, the transfer device 210 can be configured to transfer a desired amount (e.g., a predetermined amount or a user-selected amount) of bodily-fluid transferred to the first fluid reservoir 216. In some embodiments, the first, predetermined amount can substantially correspond to the size of the first fluid reservoir 216. In other embodiments, the first amount can substantially correspond to an equalization of pressure within the first fluid reservoir 216 and the portion of the patient. Moreover, in such embodiments, the equalization of the pressure can be such that the valve 260 and distal valve 221 are allowed to return to the closed configuration. Thus, the first fluid reservoir 216 can be fluidically isolated from a volume substantially outside the first fluid reservoir 216.

With the first amount is fluidically isolated, the actuator mechanism 214 can be moved from the second configuration to a third configuration by further moving the plunger 244 in the proximal direction. For example, as shown in FIG. 21, the user can apply a force to the engagement portion 268 of the plunger 244 to move the actuator mechanism 214 relative to the housing 212. As illustrated, with the at least one or a plurality of protrusions 246 of the plunger 244 engaged with the stop 250 of the pre-sample syringe tube, the further application of force on the engagement portion 268 is such that the first member 234 and the second member 236 can collectively move in the proximal direction relative to the housing 212.

The arrangement of the second member 236 within the inner volume 222 of the housing 212 is such that the proximal motion of the first member 234 and second member 236 can increase the volume of the portion of the inner volume 222 that is distal of the plunger seal 254, such that the second fluid reservoir 218 is defined. With the plunger seal 254 forming a fluid tight seal with the inner surface of the walls defining the inner volume 222 and with the valve 160 and distal valve 221 in the closed configuration, the increase of volume can produce a negative pressure within the second fluid reservoir 218.

As shown in FIG. 21, the port 220, distal valve 221 and a portion of the inner volume 222 can define a fluid flow path that places the second fluid reservoir 218 in fluid communication with the lumen-defining device. As such, the second fluid reservoir 218 can be placed in fluid communication with the portion of the patient (e.g., the vein). The negative pressure within the second fluid reservoir 218 produced by the movement of the plunger seal 254 can introduce a suction force within the portion of the patient. Thus, a bodily-fluid can be drawn through the port 220 and distal valve 221 and into the second fluid reservoir 218. In addition, the bodily-fluid contained within the second fluid reservoir 218 can be substantially free from microbes, contaminants, saline from a CVC line flush, heparin from a CVC line flush, or the like.

In some embodiments, with the desired amount of bodily-fluid disposed within the second fluid reservoir 218, the transfer device 210 can be removed from the patient, where fluid from the second fluid reservoir 218 can ultimately be expelled into a container (e.g., a vile, a test tube, a petri dish, a culture medium, a test apparatus, a cartridge designed for use with an automated, rapid microbial detection system, or the like). The withdrawn bodily-fluid can be used for any number of testing processes or procedures such as, for example, blood culture testing, real-time diagnostics, and/or PCR-based approaches.

Figure 23:
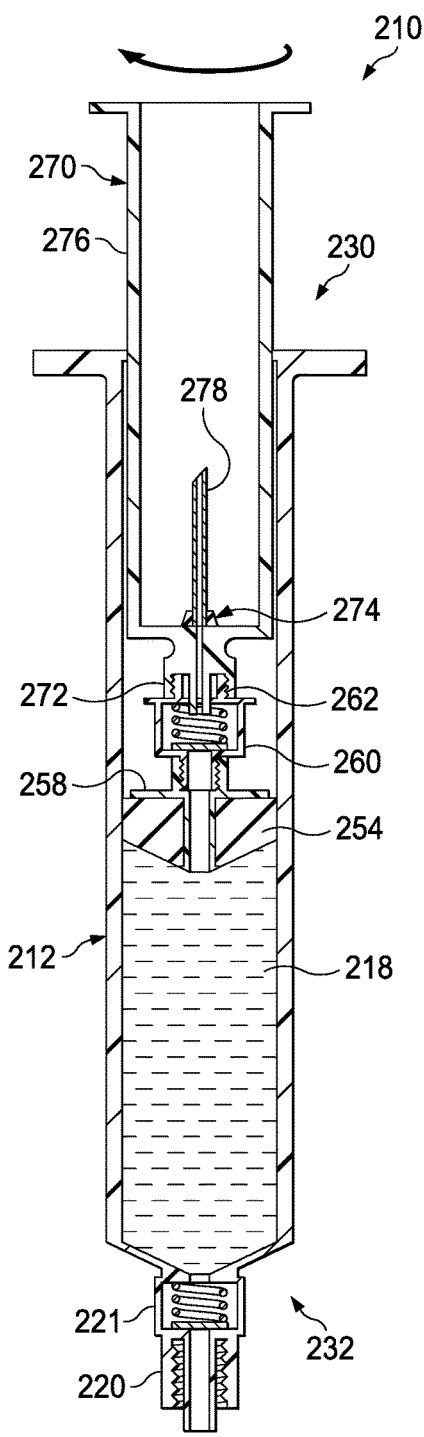
FIG. 23 depicts a cross-sectional view of the dual syringe blood collection system of FIG. 16, shown threadedly engaged with the fluid transfer adapter of FIG. 18.

To expel fluid, as shown in FIG. 22, the user can first disengage the first member 234 from the second member 236 such as, for example, by unthreading the attachment element 252 from the threaded proximal end 262 of the valve 260. Once the first member has been detached, and as shown in FIG. 23, the fluid transfer adapter 270 can be selectively engaged with the second member 236 of the transfer device 210. For example, the fluid transfer adapter 270 can include an attachment element 272 that can threadedly engage the threaded proximal end 262 of the valve 260. In such a manner the fluid transfer adapter 270 can be in fluid communication with the fluid sample retained within the second fluid reservoir 218. The attachment element 272 can have a similar structure and function as port 220, where the attachment element 272 can include a transfer valve or can lack such a valve. If such a valve is present it can be a one-way check valve that be monolithically formed with the attachment element 272 and/or with the fluid transfer adapter 270.

The fluid transfer adapter 270 can be any suitable fluid transfer device or component. In one embodiment, the fluid transfer adapter 270 can be a BD VACUTAINER LUER-LOK access device. The fluid transfer adapter 270 can include a needle assembly 274 for collecting multiple samples of fluid from a patient with an anti-backflow valve. The fluid transfer adapter 270 can facilitate the transfer of the sample from the second fluid reservoir 218 into a vacuum collection device 299 or any other suitable container or the like. The fluid transfer adapter 270 can include a housing 276, a needle assembly 274 retained within a cavity defined by the housing 276, where the needle assembly 274 can include a shrouded needle cannula 278 for penetration of a vacuum collection device 299 for collection of a blood sample.

Figure 24:
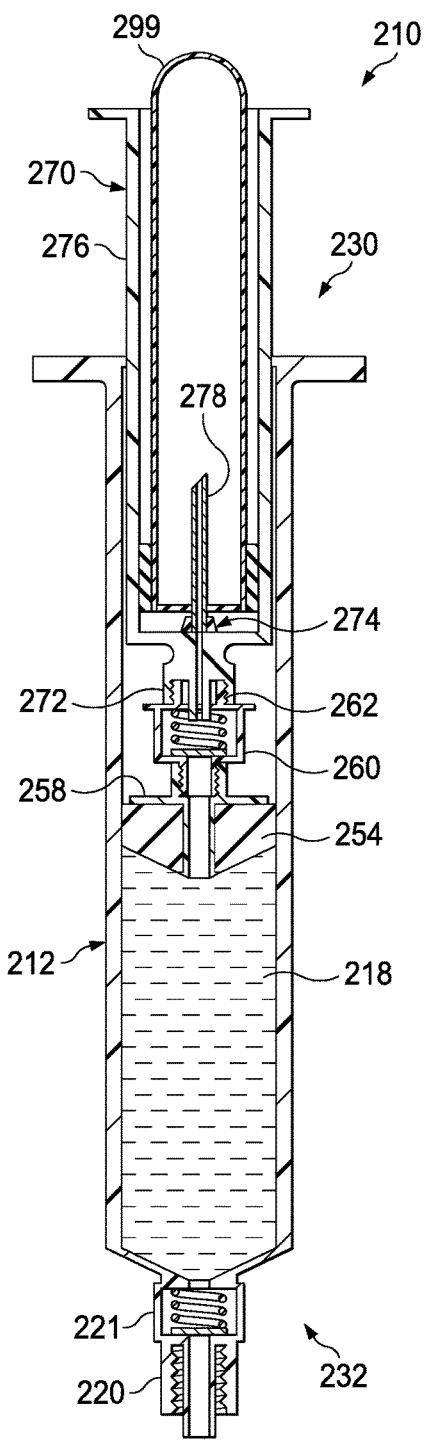
FIG. 24 depicts a cross-sectional view of the dual syringe blood collection system of FIG. 16 shown a fluid receptacle engaged with the fluid transfer adapter.
Figure 25:
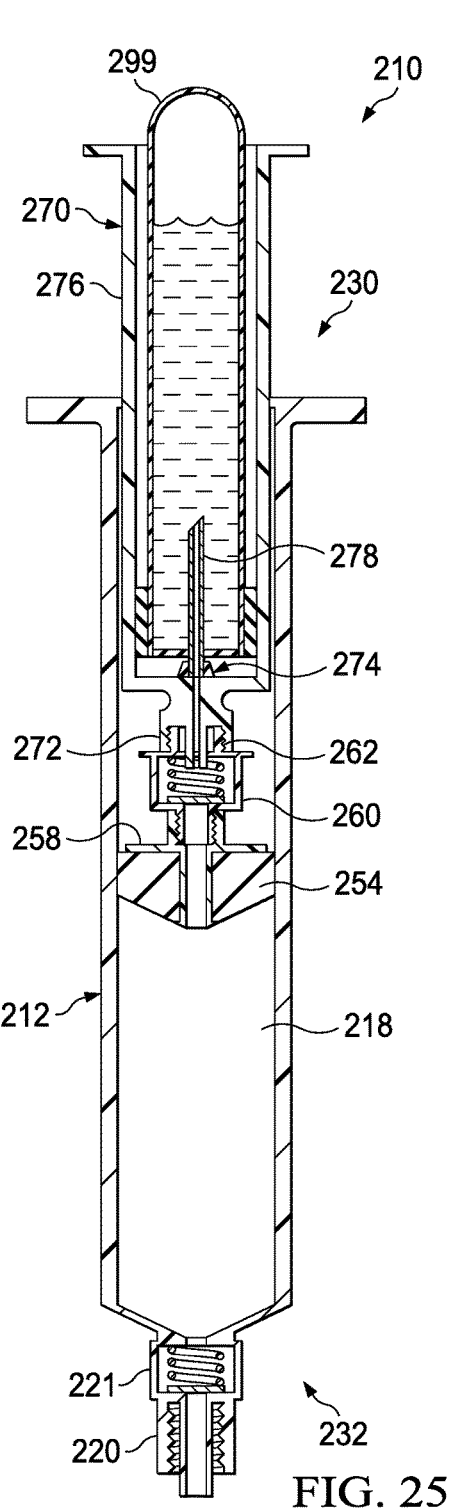
FIG. 25 depicts a cross-sectional view of the dual syringe blood collection system of FIG. 16 shown with the sample being urged from the second reservoir into the fluid receptacle of FIG. 24.
Figure 26:
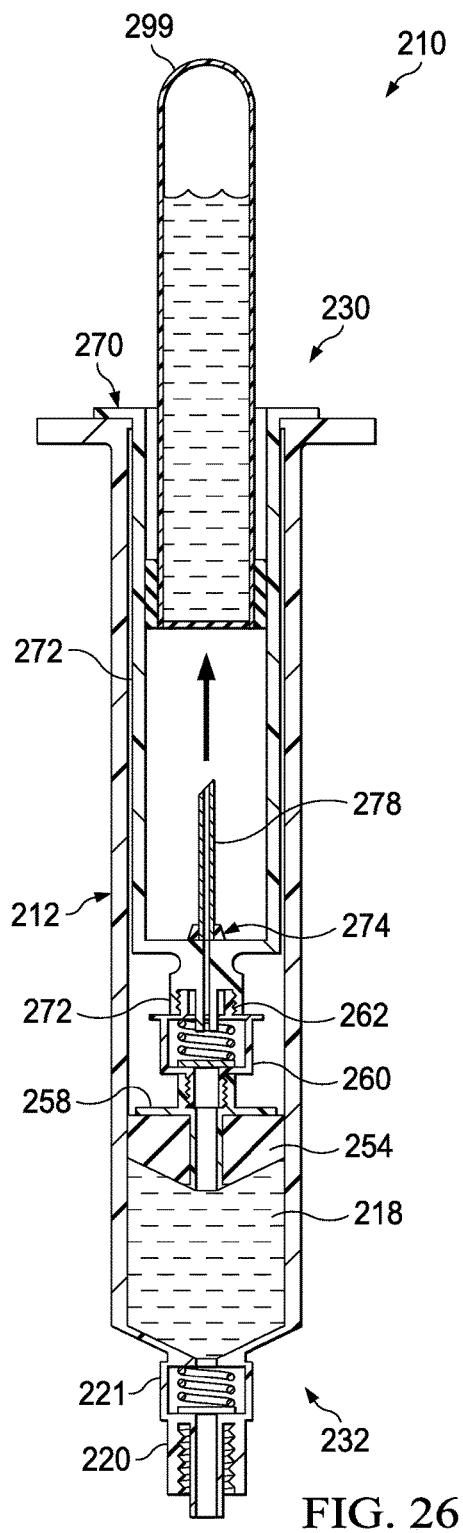
FIG. 26 depicts a cross-sectional view of the dual syringe blood collection system of FIG. 16 shown with the filled fluid receptacle of FIG. 24 removed.

As shown in FIG. 24, once the vacuum collection device 299, or the like, has been attached to the fluid transfer adapter 270 it can be in fluid communication with the second fluid reservoir 218. Negative pressure within the vacuum collection device 299 can draw the fluid sample into the container for testing or any other suitable purposes. In an alternate embodiment, the fluid transfer adapter 270 can be depressed or advanced distally relative to the housing 212 to urge fluid from the second fluid reservoir 218 into any suitable container. Although not described in detail with respect to this embodiment, it will be appreciated that the removed first member 234 containing the first fluid reservoir 216 can be used for any suitable purpose such as, for example, an autologous transfusion, as shown and described in accordance with other embodiments.

FIGS. 27-35 illustrate a syringe-based transfer device 310 according to an embodiment. The syringe-based transfer device 310 (also referred to herein as "bodily-fluid transfer device," "fluid transfer device," or "transfer device") includes a housing 312 and an actuator mechanism 314. The transfer device 310 can be configured to include or define a first fluid reservoir 316 (also referred to herein as "first reservoir" or "pre-sample reservoir") and a second fluid reservoir 318 (also referred to herein as "second reservoir" or "sample reservoir"). The transfer device 310 can be any suitable shape, size, or configuration. For example, while shown in FIG. 27 as being substantially cylindrical, the transfer device 310 can be square, rectangular, polygonal, and/or any other non-cylindrical shape.

Figure 27:
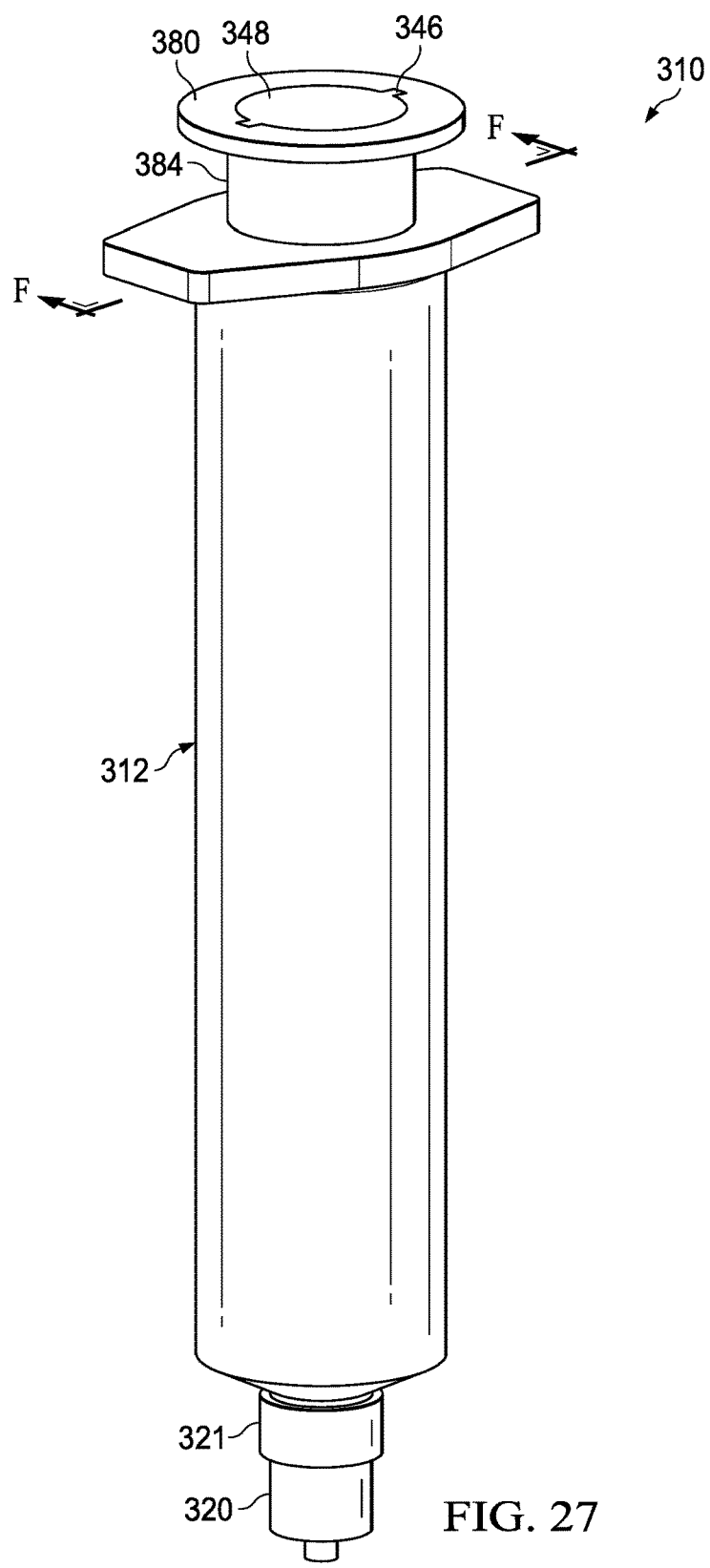
FIG. 27 depicts a perspective view of a fluid collection system in accordance with a "closed system" having an integrated fluid transfer adapter according to one embodiment.
Figure 28:
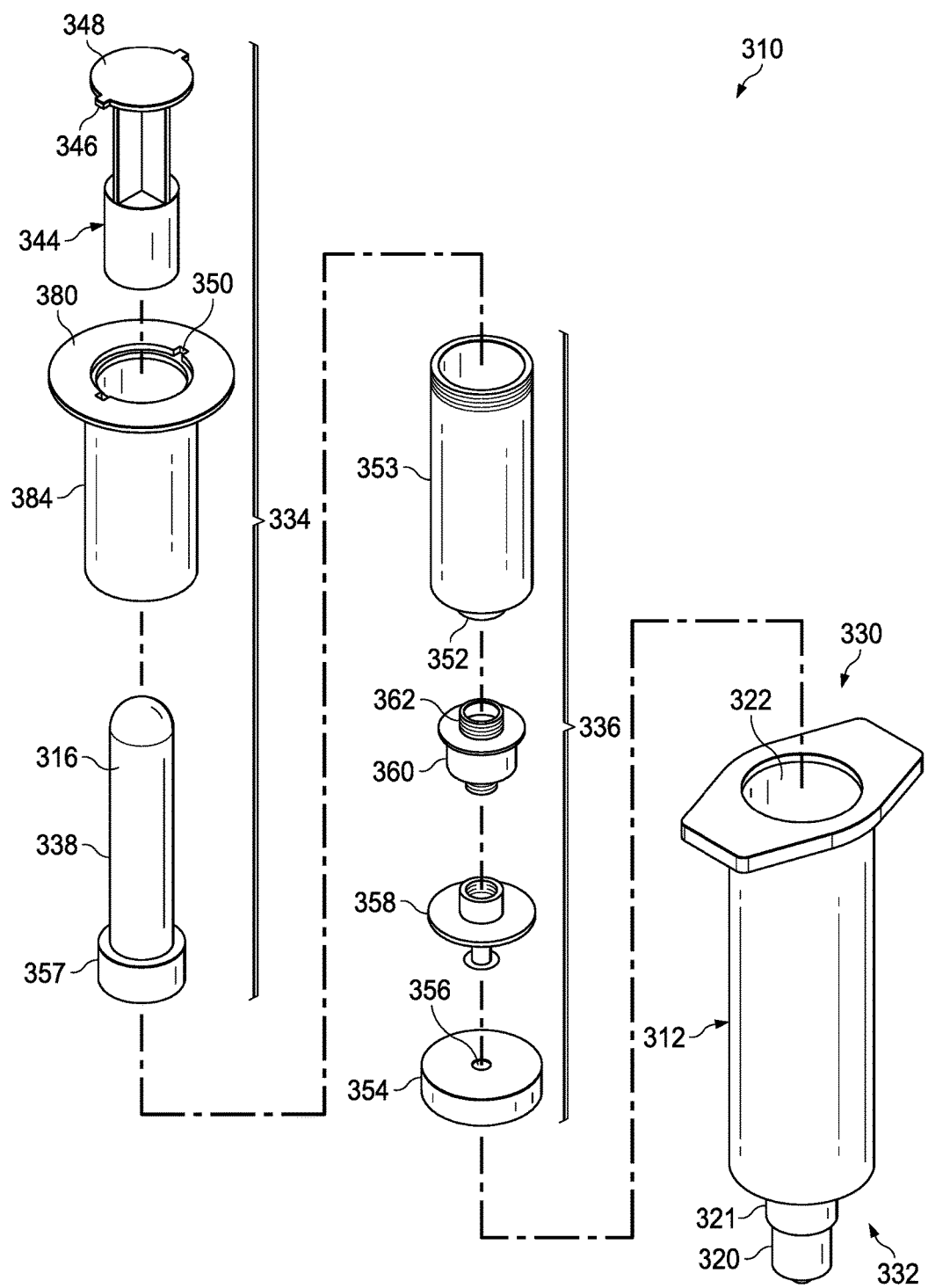
FIG. 28 depicts an exploded view of the fluid collection system shown in FIG. 27.
Figure 29:
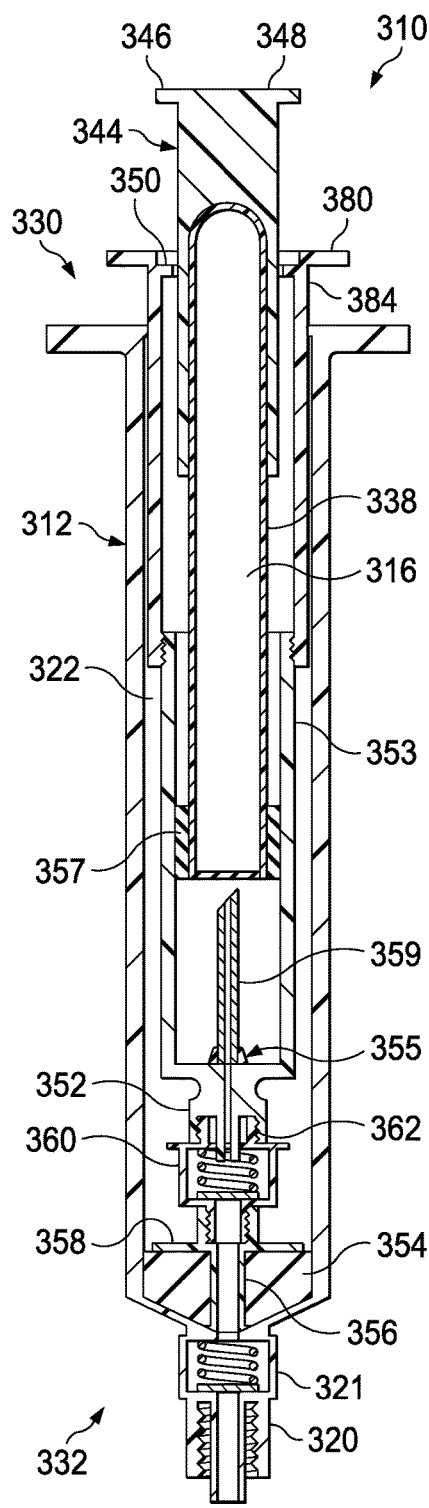
FIG. 29 depicts a cross-sectional view of the fluid collection system of FIG. 27, taken along reference line F-F and shown in a pre-use configuration.

As shown in FIGS. 27 and 28, the housing 312 can include a proximal end portion 330 and a distal end portion 332 and can define an inner volume 322 therebetween. In some embodiments, the housing 312 can be substantially similar to a syringe body. The proximal end portion 330 of the housing 312 can be substantially open and can be configured to receive at least a portion of the actuator mechanism 314 such that at least the portion of the actuator mechanism 314 can be movably disposed within the inner volume 322. Furthermore, the inner volume 322 can be configured to define the second fluid reservoir 318, as further described herein. The distal end portion 332 of the housing 312 can include a port 320. In some embodiments, the port 320 can be monolithically formed with the housing 312 (e.g., as shown in FIG. 27). In other embodiments, the port 320 can be coupled to the distal end portion 332 in any suitable manner such as, for example, via a friction fit, a threaded coupling, a mechanical fastener, an adhesive, any number of mating recesses, and/or any combination thereof. The port 320 can include a distal valve 321, where the distal valve can be a one-way check valve similar in design and operation to the distal valve 221 as described with reference to FIGS. 16 and 17.

The port 320 can be any suitable shape, size, or configuration. For example, in some embodiments, at least a portion of the port 320 can form a lock mechanism configured to be physically and fluidically coupled to a Central Venous Catheter (CVC) line, a PICC lines, a needle, a cannula, or other lumen-containing device. For example, in some embodiments, the port 320 can be a LUER-LOK or similar locking mechanism that can be configured to physically and fluidically couple to a CVC line (not shown). In other embodiments, the port 320 can be monolithically formed in a unitary, one piece construction with at least a portion of the lumen-containing device. In this manner, the port 320 can be placed in fluid communication with a lumen defined by the lumen-defining device and to receive the bodily-fluid from a patient when the lumen-defining device is disposed within the patient.

The actuator mechanism 314 can be disposed within the inner volume 322 and at least a portion can be movable between a first configuration (e.g., a proximal position relative to the housing 312) and a second configuration (e.g., a distal position relative to the housing 312). The movement of the actuator mechanism 314 relative to the housing 312 can move the transfer device 310 between a number of different configurations and positions, as further described herein. The actuator mechanism 314 can include a first member 334 and a second member 336. The first member 334 of the actuator mechanism 314 can include a plunger 344, a selectively removable plunger cap 384, and a pre-sample container 338 that can define a first fluid reservoir 316. The pre-sample container 338 can be, for example, a VACUTAINER blood collection tube having a sterile glass tube with a colored rubber stopper for creating a vacuum seal inside of the pre-sample container 338. The pre-sample container 338 can facilitate the draw of a predetermined volume of liquid and can be fluidically sealed to define the first fluid reservoir 316. In certain embodiments, the first fluid reservoir can have a defined volume. The plunger 344 can initially be configured to translate relative to the selectively removable plunger cap 384.

The pre-sample container 338 can include a closed proximal end that can be engaged by a portion of the plunger 344, such as a distal end of the plunger 144, such that distal actuation of the plunger 344 can correspondingly advance the pre-sample container 338 distally where, for example, the distal end of the plunger 144 can be operably coupled or connected with the pre-sample container 338. The plunger 344 can include one or a plurality of protrusions 346 (or at least one projection) that can extend radially or laterally outward from a first plunger flange 348 at the proximal end of the plunger 344 such that the one or a plurality of protrusions 346 can be configured to mate with a catch 350 positioned on a proximal end 380 of the selectively removable plunger cap 384. The one or a plurality of protrusions 346 can be fixedly coupled with the catch 350, where the protrusions 346 can engage the catch 350 in a snap fit, such that the plunger 344 and selectively removable plunger cap 384 are locked such that relative movement between the components cannot occur. In this manner, the one or a plurality of protrusions 346 and the catch 350 can be placed in contact to substantially limit a proximal movement of the plunger 344 relative to the selectively removable plunger cap 384 once the one or a plurality of protrusions 346 have engaged the catch 350. The relative position of the one or a plurality of protrusions 346 can be set such that the first member 334 can be urged distally to securely engage a shrouded cannula assembly 355 of the second member 336 as will be described in more detail herein. It will be appreciated that any suitable mechanism of engagement is contemplated, including reversing the illustrated components, where such engagement can result in a fixed or selectively detachable coupling.

The second member 336 can include a plunger seal 354 that can form a friction fit with the inner surface of the walls defining the inner volume 322 when the actuator mechanism 314 is disposed within the housing 312. Similarly stated, the plunger seal 354 can define a fluidic seal with the inner surface of the walls defining the inner volume 322 such that a portion of the inner volume 322 distal of the plunger seal 354 is fluidically isolated from a portion of the inner volume 322 proximal of the plunger seal 354. The plunger seal 354 can define a channel 356 that that can extend through a distal end and a proximal end of the plunger seal 354. A portion of an inner set of walls defining the channel 356 can accept a valve seat 358. In this manner, a portion of the channel 356 can receive a valve 360 that is in contact with the valve seat 358. The valve 360 can include a threaded proximal end 362 that can selectively engage an attachment element 352 on a threaded plunger tube 353. The threaded plunger tube 353 can include a shrouded cannula assembly 355 that can be fixedly coupled with the threaded plunger tube 353 and can project proximally into a cavity defined by the threaded plunger tube 353. The threaded plunger tube 353 of the second member 336 can be threadedly engaged with the selectively removable plunger cap 384 such that the first member 334 can be disengaged from the second member 336. It will be appreciated that any suitable engagement between the removable cap and the plunger tube is contemplated including, for example, a snap fit, a latch, a push fit, a rotational locking mechanism, an outwardly biased flexible hinge that engages a stop, or the like. For example, the removable cap can include a first coupling member that can engage a second coupling member of the plunger tube.

The valve 360 can be any suitable valve. For example, in some embodiments, the valve 360 can be a one-way check valve to allow a flow of a fluid from a distal end of the valve 360 to a proximal end of the valve 360, but substantially not allow a flow of the fluid from the proximal end to the distal end. The valve 360 can be disposed within the channel 356 and can be in contact with the valve seat 358 such that the valve 360 forms a substantially fluid tight seal with the walls defining the channel 356. In some embodiments, the valve 360 can form a friction fit with walls defining the channel 356. In other embodiments, the valve 360 can form a threaded coupling or the like with at least a portion of the walls. The valve 360 can also include a seal member configured to engage the valve seat 358 to form at least a portion of the fluid tight seal.

As described above, the second member 336 can be movably disposed within the housing 312. More specifically, the second member 336 can be movable between a second configuration (e.g., a distal position) and a third position (e.g., a proximal position) to create a vacuum or negative pressure to draw a sample into the second fluid reservoir 318.

In use, as shown in FIGS. 29-35 a user can engage the transfer device 310 to couple the port 320 to a proximal end portion of a lumen-defining device (not shown) such as, for example, a CVC line, a PICC line, a butterfly needle, a cannula assembly, a trocar (which is some cases is used to insert a catheter into a patient), or the like. With the port 320 physically coupled to the lumen-defining device, the port 320 can be placed in fluid communication with the lumen defined by the lumen-defining device. The distal end portion of the lumen-defining device can be disposed within a portion of the body of a patient (e.g., a vein). In this manner, the port 320 is placed in fluid communication with the portion of the body.

Figure 30:
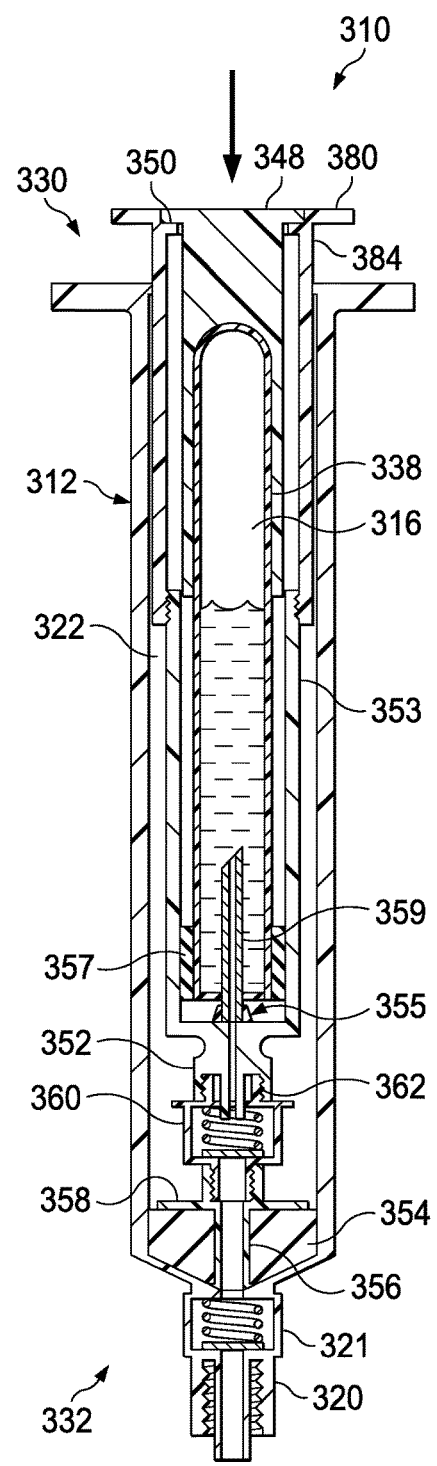
FIG. 30 depicts a cross-sectional view of the fluid collection system of FIG. 27, shown with a plunger advanced distally and a pre-sample drawn into a first reservoir of a pre-sample container.

As shown in FIG. 30 with the port 320 coupled to the lumen-defining device, a user (e.g., a phlebotomist, a nurse, a technician, a physician, or the like) can move the transfer device 310 from a first configuration to a second configuration. More specifically, the user distally push or advance the first plunger flange 348 of the plunger 344 to engage the one or a plurality of protrusions 346 with the catch 350 or stop and to concomitantly engage a distal stopper 357 of the pre-sample container 338 with the shrouded cannula assembly 355, such that the cannula 359 can penetrate the distal stopper 357. Engaging the pre-sample container 338 with the cannula 359 can fluidly couple the first fluid reservoir 316 defined by the pre-sample container 338 with the cannula 359 and valve 360. The pre-sample container 338 can create a negative pressure or a vacuum within the first fluid reservoir 316. As shown in FIG. 30, the negative pressure in the first fluid reservoir 316 can draw fluid, such as a pre-sample of blood from a patient, into the first fluid reservoir 316. The first fluid reservoir 316 can be sized such that a predetermined amount of pre-sample fluid, such as "waste" blood, will fill the pre-sample container 338.

The arrangement of the plunger 344 within the pre-sample container 338 can be such that the proximal motion of the plunger 344 can facilitate engagement between the pre-sample container 338 and the cannula 359 such that access to the first fluid reservoir 316 provided. For example, the cannula 359 can pierce the distal stopper 340 such that the cannula is in fluid communication with the first fluid reservoir 316. With the distal stopper 340 forming a fluid tight seal around the cannula 359, the negative pressure within the pre-sample container 338 can draw fluid into the first fluid reservoir 316.

As shown in FIG. 30, the port 320, the channel 356, the valve 360, the attachment element 352, and the shrouded cannula assembly 355 can define a fluid flow path that places the first fluid reservoir 316 in fluid communication with the lumen-defining device. Therefore, the first fluid reservoir 316 can correspondingly be placed in fluid communication with the portion of the patient (e.g., the vein). The negative pressure within the first fluid reservoir 316 can be operative in moving the valve 360 from a closed configuration to an open configuration. In this manner, the negative pressure within the within the first fluid reservoir 316 can introduce a suction force within the portion of the patient. A bodily-fluid can be drawn through the port 320 and the valve 360, through the attachment element 352, through the cannula 359, and into the first fluid reservoir 316. In some embodiments, the bodily-fluid can contain undesirable microbes or contaminant such as, for example, sub-dermal microbes, saline associated with a CVC flush, heparin associated with a CVC flush, or the like.

While in the second configuration, the transfer device 310 can be configured to transfer a desired amount (e.g., a predetermined amount or a user-selected amount) of bodily-fluid transferred to the first fluid reservoir 316. In some embodiments, the first, predetermined amount can substantially correspond to the size of the first fluid reservoir 316. In other embodiments, the first amount can substantially correspond to an equalization of pressure within the first fluid reservoir 316 and the portion of the patient. Moreover, in such embodiments, the equalization of the pressure can be such that the valve 360 is allowed to return to the closed configuration.

Figures 31, 32:
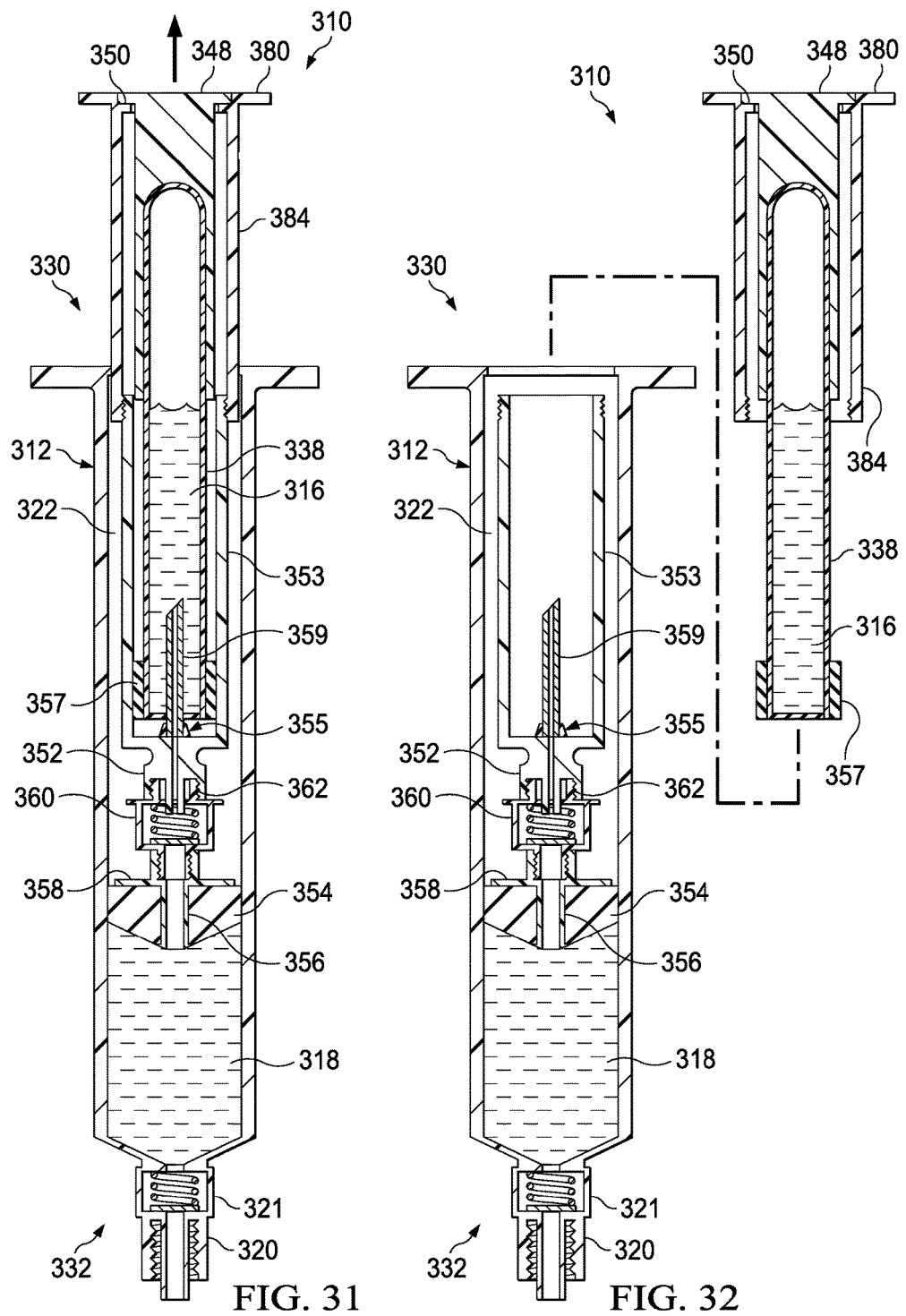
FIG. 31 depicts a cross-sectional view of the fluid collection system of FIG. 27, shown with an actuator mechanism urged proximally such that a fluid sample is drawn into a second reservoir.
FIG. 32 depicts a cross-sectional view of the fluid collection system of FIG. 27, shown with a first member of the actuator mechanism, including the first fluid reservoir, selectively detached from a second member of the actuator mechanism.

With the first amount fluidically isolated, the actuator mechanism 314 can be moved from the second configuration to a third configuration by moving the selectively removable plunger cap 384 and coupled plunger 344 in the proximal direction. For example, as shown in FIG. 31, the user can apply a force to the selectively removable plunger cap 384 to move the actuator mechanism 314 relative to the housing 312 in a proximal direction. The application of force in a proximal direction can be such that the first member 334 and the second member 336 collectively move in the proximal direction relative to the housing 312.

The arrangement of the second member 336 within the inner volume 322 of the housing 312 can be such that the proximal motion of the first member 334 and second member 336 increases the volume of the portion of the inner volume 322 that is distal of the plunger seal 354, such that the second fluid reservoir 318 is defined. With the plunger seal 354 forming a fluid tight seal with the inner surface of the walls defining the inner volume 322 and with the valve 360 in the closed configuration, the increase of volume can produce a negative pressure within the second fluid reservoir 318.

As shown in FIG. 31, the port 320 and a portion of the inner volume 322 can define a fluid flow path that places the second fluid reservoir 318 in fluid communication with the lumen-defining device. As such, the second fluid reservoir 318 can be placed in fluid communication with the portion of the patient (e.g., the vein). The negative pressure within the second fluid reservoir 318 produced by the movement of the plunger seal 354 can introduce a suction force within the portion of the patient. Thus, a bodily-fluid can be drawn through the port 320 and into the second fluid reservoir 318. In addition, the bodily-fluid contained within the second fluid reservoir 318 can be substantially free from sub-dermal microbes, contaminants, saline from a CVC line flush, heparin from a CVC line flush, or the like.

To expel fluid, as shown in FIG. 32, the user can first disengage the selectively removable plunger cap 384 from the threaded plunger tube 353 such as, for example, by unthreading the selectively removable plunger cap 384 from the threaded plunger tube 353. Once the first member 334 has been detached, and as shown in FIG. 32, the pre-sample container 338 can be accessible via an open proximal end of the threaded plunger tube 353. A clinician can grasp or otherwise pull the pre-sample container 338 proximally to remove the cannula 359 from inside the first fluid reservoir 316. In certain embodiments the threaded plunger tube 353 and the pre-sample container 338 can be coupled such that removing the threaded plunger tube 353 correspondingly removes the pre-sample container 338. The distal stopper 357 can seal upon removal of the cannula 359 such that the first fluid reservoir 316 is again fluidically sealed. The pre-sample container 338 can be removed from the transfer device 310 and used for testing, or the like, in accordance with embodiments described herein. It will be appreciated that the pre-sample container 338 can be a syringe or other device that can permit the fluid sample to be expelled for testing, an autologous transfusion, or the like.

Figure 33:
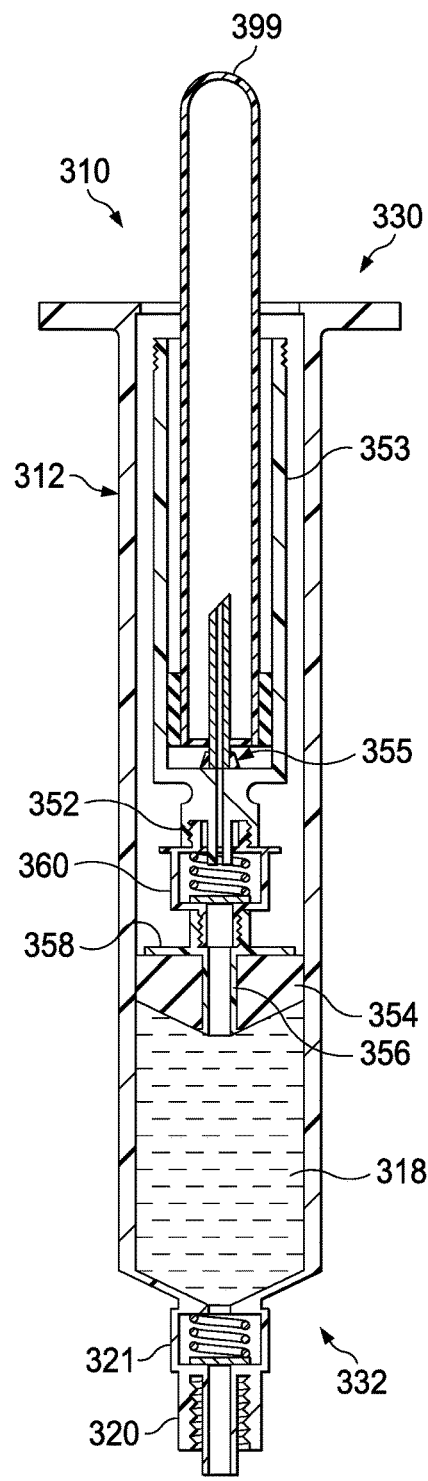
FIG. 33 depicts a cross-sectional view of the fluid collection system of FIG. 27 shown with a collection vial engaged with a shrouded cannula assembly of the second member.
Figure 34:
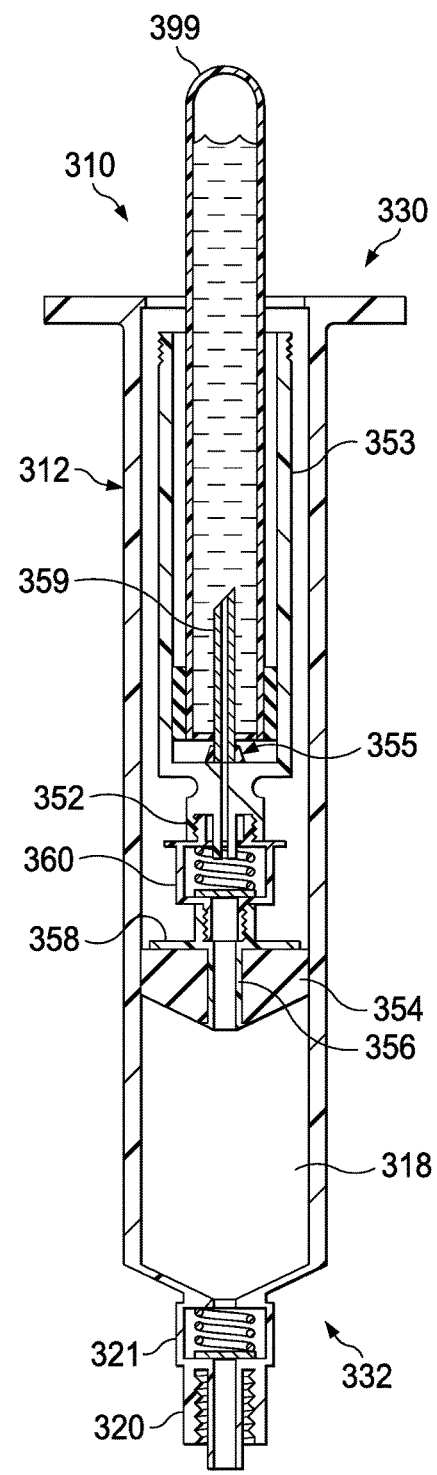
FIG. 34 depicts a cross-sectional view of the fluid collection system of FIG. 27 shown with the sample being urged from the second fluid reservoir into the collection vial of FIG. 33.
Figure 35:
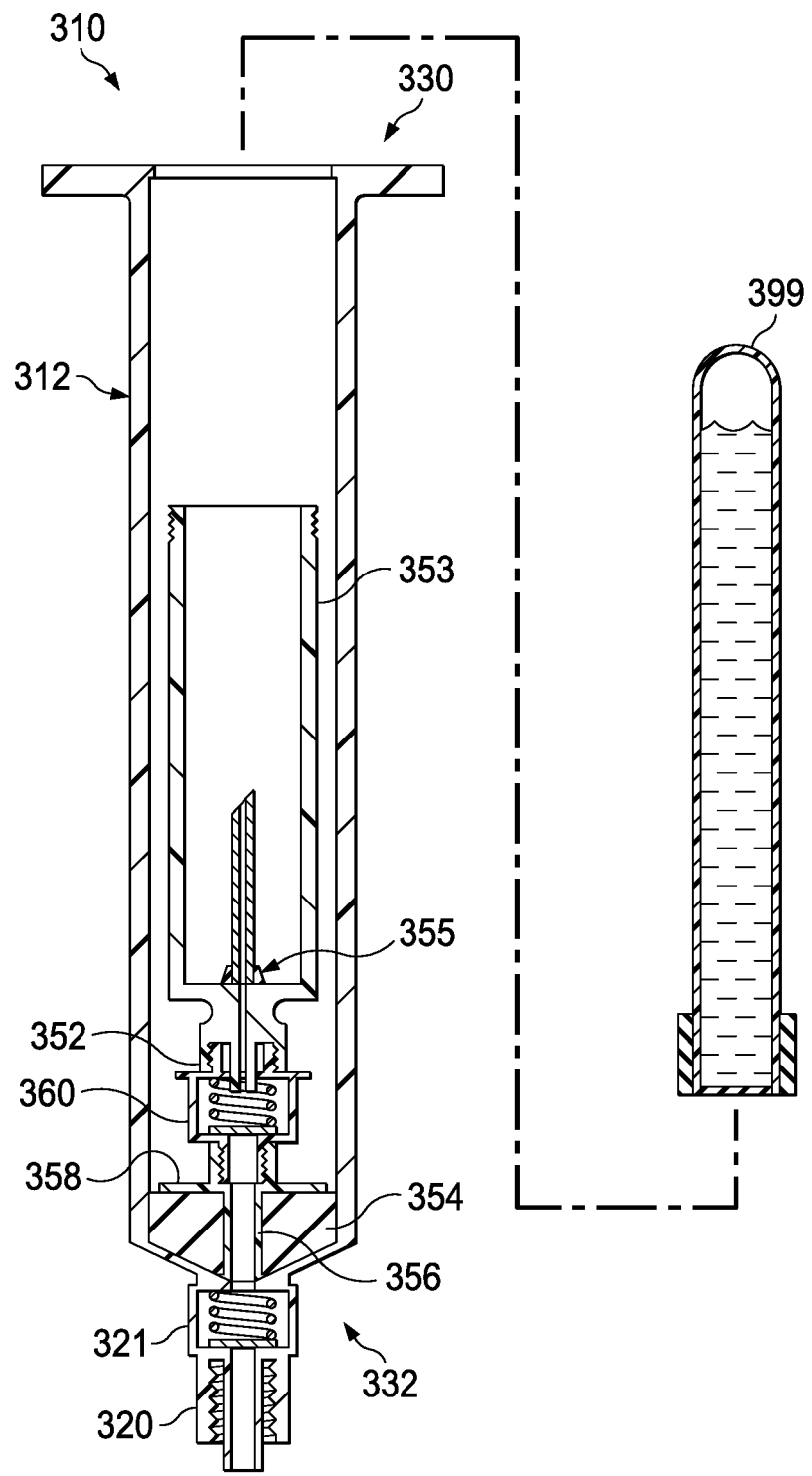
FIG. 35 depicts a cross-sectional view of the fluid collection system of FIG. 27 shown with the filled collection vial of FIG. 33 removed.
Figure 36:
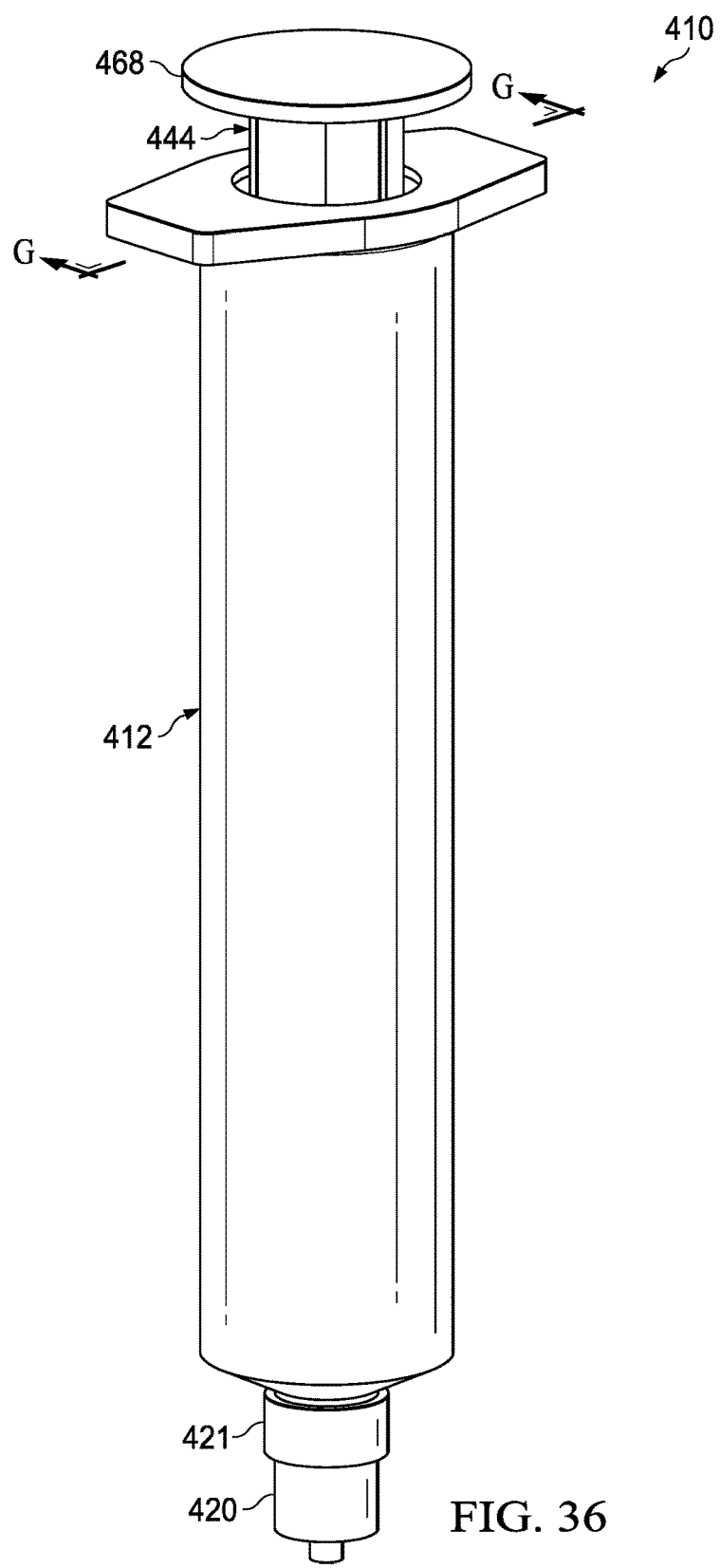
FIG. 36 depicts a perspective view of a fluid collection system in accordance with a "closed system" having an integrated fluid transfer adapter according to one embodiment.

The shrouded cannula assembly 355 can be any suitable fluid transfer device or component. In one embodiment, the threaded plunger tube 353 and the shrouded cannula assembly 355 can function in a manner substantially similar to the fluid transfer adapter 270 described with respect to FIGS. 16 and 17. The shrouded cannula assembly 355 can be used for collecting multiple samples of fluid from a patient with an anti-backflow valve, such as transfer valve. As shown in FIG. 33, a vacuum collection device 399 can be selectively coupled with the shrouded cannula assembly 355. The shrouded cannula assembly 355 can facilitate the transfer of the sample from the second fluid reservoir 318 into the vacuum collection device 399 as shown in FIG. 34. Once the vacuum collection device 399 has been attached to the shrouded cannula assembly 355 it can be in fluid communication with the second fluid reservoir 318. Negative pressure within the evacuated container can draw the fluid sample into the vacuum collection device 399 for testing or any other suitable purposes. As illustrated in FIG. 35, the vacuum collection device 399 can be selectively removed from the threaded plunger tube 353 and cannula 359.

FIGS. 37-43 illustrate a syringe-based transfer device 410 according to an embodiment. The syringe-based transfer device 410 (also referred to herein as "bodily-fluid transfer device," "fluid transfer device," or "transfer device") includes a housing 412 and an actuator mechanism 414. The transfer device 410 can be any suitable shape, size, or configuration. For example, while shown in FIG. 37 as being substantially cylindrical, the transfer device 410 can be square, rectangular, polygonal, and/or any other non-cylindrical shape.

Figure 37:
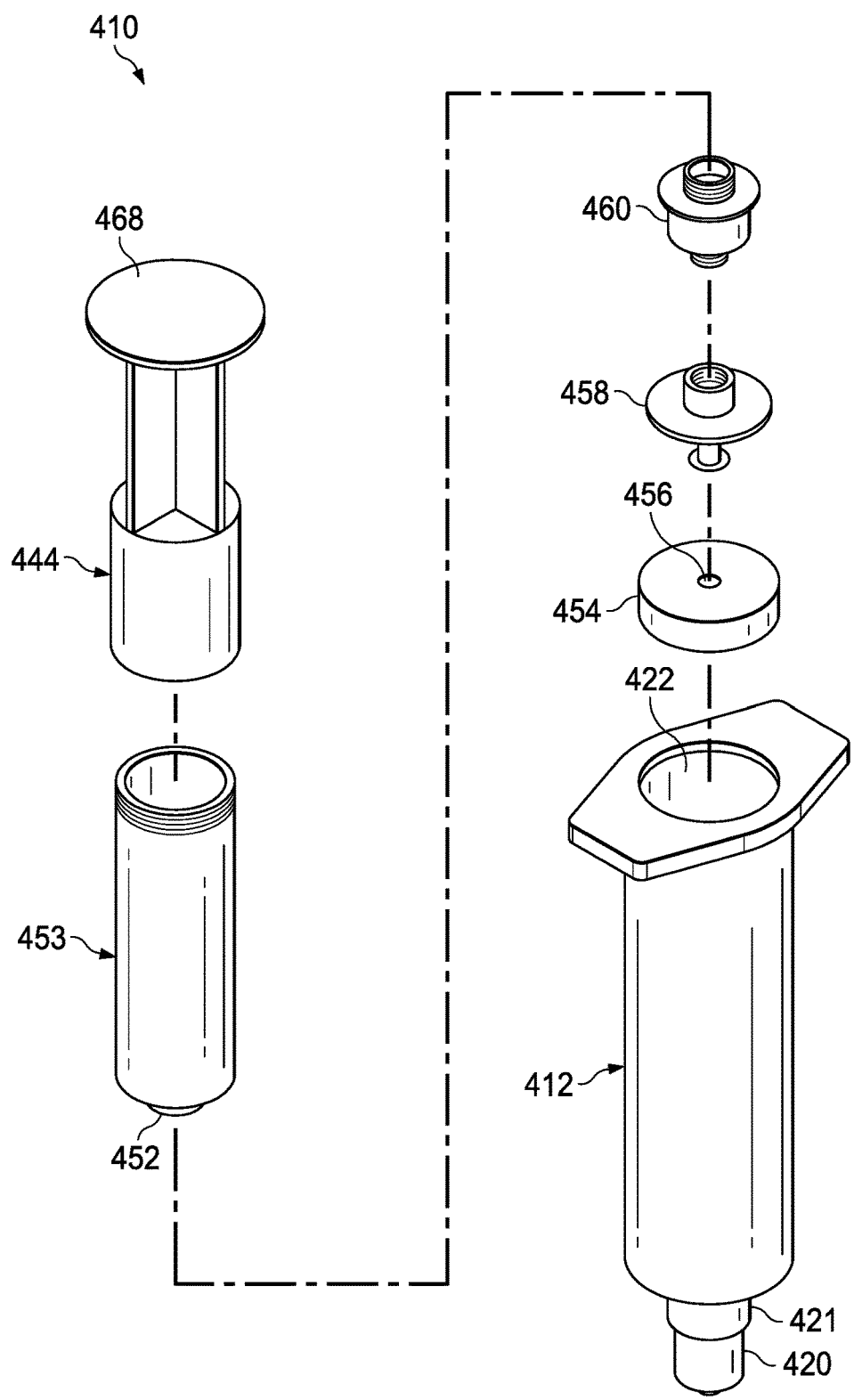
FIG. 37 depicts an exploded view of the fluid collection system shown in FIG. 36.
Figure 38:
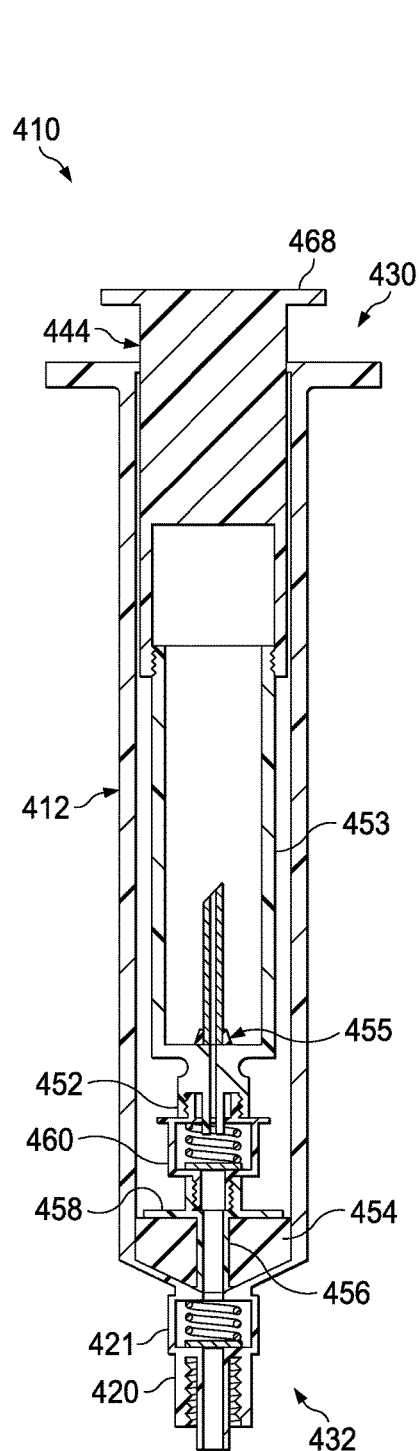
FIG. 38 depicts a cross-sectional view of the fluid collection system of FIG. 36, taken along reference line G-G and shown in a pre-use configuration.

As shown in FIG. 37, the housing 412 can include a proximal end portion 430 and a distal end portion 432 and can define an inner volume 422 therebetween. In some embodiments, the housing 412 can be substantially similar to a syringe body. The proximal end portion 430 of the housing 412 can be substantially open and can be configured to receive at least a portion of the actuator mechanism 414 such that at least the portion of the actuator mechanism 414 can be movably disposed within the inner volume 422. Furthermore, the inner volume 422 can be configured to define a fluid reservoir 418, as further described herein. The distal end portion 432 of the housing 412 can include a port 420. In some embodiments, the port 420 can be monolithically formed with the housing 412 (e.g., as shown in FIG. 37). In other embodiments, the port 420 can be coupled to the distal end portion 432 in any suitable manner such as, for example, via a friction fit, a threaded coupling, a mechanical fastener, an adhesive, any number of mating recesses, and/or any combination thereof. The port 420 can include a distal valve 421, where the distal valve 421 can be any suitable valve. For example, in some embodiments, the distal valve 421 can be a one-way check valve to allow a flow of a fluid from a distal end of the distal valve 421 to a proximal end of the distal valve 421, but substantially not allow a flow of the fluid from the proximal end to the distal end.

The port 420 can be any suitable shape, size, or configuration. For example, in some embodiments, at least a portion of the port 420 can form a lock mechanism configured to be physically and fluidically coupled to a Central Venous Catheter (CVC) line, a PICC lines, a needle, a cannula, or other lumen-containing device. For example, in some embodiments, the port 420 can be a LUER-LOK or similar locking mechanism that can be configured to physically and fluidically couple to a CVC line (not shown). In other embodiments, the port 420 can be monolithically formed in a unitary, one piece construction with at least a portion of the lumen-containing device. In this manner, the port 420 can be placed in fluid communication with a lumen defined by the lumen-defining device and to receive the bodily-fluid from a patient when the lumen-defining device is disposed within the patient.

The actuator mechanism 414 can be disposed within the inner volume 422 and at least a portion can be movable between a first position (e.g., a distal position relative to the housing 412) and a second position (e.g., a proximal position relative to the housing 412). The movement of the actuator mechanism 414 relative to the housing 412 can move the transfer device 410 between a number of different configurations and positions, as further described herein. The actuator mechanism 414 can include a plunger 444 that can be selectively engaged with a plunger tube 453. In the illustrated embodiment the plunger 444 and the plunger tube 453 can be threadedly engaged, but it will be appreciated that any suitable coupling is contemplated. The plunger tube 453 can be coupled and/or disengaged from the plunger 444 in any suitable manner such as, for example, a snap fit, a latch, a push fit, a rotational locking mechanism, or the like.

The actuator mechanism 414 can include a plunger seal 454 that can form a friction fit with the inner surface of the walls defining the inner volume 422 when the actuator mechanism 414 is disposed within the housing 412. Similarly stated, the plunger seal 454 can define a fluidic seal with the inner surface of the walls defining the inner volume 422 such that a portion of the inner volume 422 distal of the plunger seal 454 is fluidically isolated from a portion of the inner volume 422 proximal of the plunger seal 454. The plunger seal 454 can define a channel 456 that that can extend through a distal end and a proximal end of the plunger seal 454. A portion of an inner set of walls defining the channel 456 can accept a luer adapter 458. The luer adapter 458 can operably couple the plunger seal 454 with the plunger tube 453. In the illustrated embodiment, a valve 460 can be used to couple the plunger tube 453 with the luer adapter 458, where the valve 460 can be a one-way check valve that can prevent fluid from flowing distally out of the valve 460. In embodiments where the valve 460 is unnecessary it may be absent or selectively removable such as by unthreading the valve from the luer adapter 458. The luer adapter 458 can also be monolithically formed in a one-piece, unitary construction with the plunger tube 453. In certain embodiments, the plunger tube 453 can include a distal attachment member 452, which can be a threaded LUER-LOK, for attachment to the luer adapter 458. The plunger tube 453 can include a shrouded cannula assembly 455 that can be fixedly coupled with the plunger tube 453 and can project proximally into a cavity defined by the plunger tube 453.

As described above, the actuator mechanism 414 can be movably disposed within the housing 412. More specifically, the actuator mechanism 414 can be movable between a first configuration (e.g., a distal position) and second configuration (e.g., a proximal position) to create a vacuum or negative pressure to draw a sample into the fluid reservoir 418.

In use, as shown in FIGS. 38-43, a user can engage the transfer device 410 to couple the port 420 and distal valve 421 to a proximal end portion of a lumen-defining device (not shown) such as, for example, a CVC line, a PICC line, a butterfly needle, a cannula assembly, a trocar (which is some cases is used to insert a catheter into a patient), or the like. With the port 420 physically coupled to the lumen-defining device, the port 420 and distal valve 421 can be placed in fluid communication with the lumen defined by the lumen-defining device. The distal end portion of the lumen-defining device can be disposed within a portion of the body of a patient (e.g., a vein). In this manner, the port 420 can be placed in fluid communication with the portion of the body.

Figure 39:
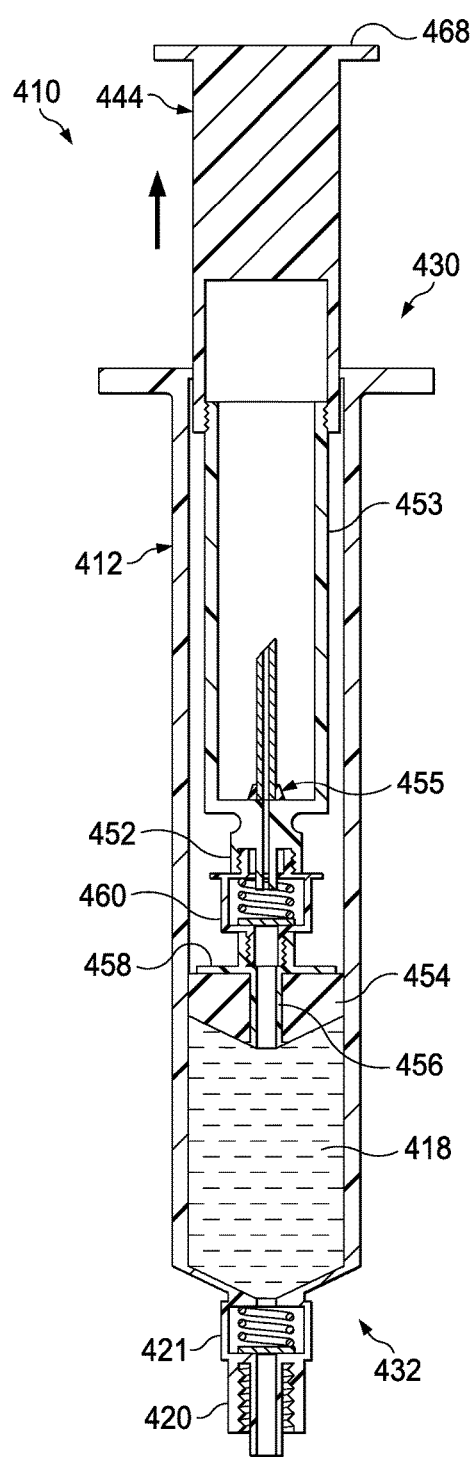
FIG. 39 depicts a cross-sectional view of the fluid collection system of FIG. 36, shown with an actuator mechanism urged proximally such that a fluid sample is drawn into a reservoir.

With the port 420 coupled to the lumen-defining device, a user (e.g., a phlebotomist, a nurse, a technician, a physician, or the like) can move the transfer device 410 from the first position to the second position. As shown in FIG. 39, the actuator mechanism 414 can be moved from the first configuration to the second configuration by moving the plunger 444 and plunger tube 453, which are coupled together, in the proximal direction. The arrangement of actuator mechanism 414 within the inner volume 422 of the housing 412 can be such that the proximal motion of the actuator mechanism 414 increases the volume of the portion of the inner volume 422 that is distal of the plunger seal 454, such that the fluid reservoir 418 is defined. With the plunger seal 454 forming a fluid tight seal with the inner surface of the walls defining the inner volume 422, the increase of volume can produce a negative pressure within the fluid reservoir 418.

Figure 41:
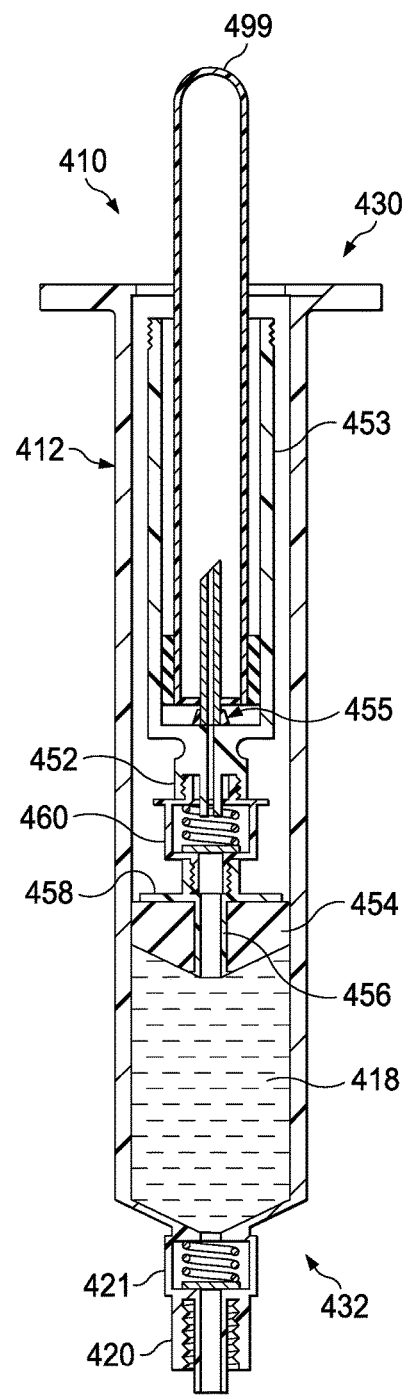
FIG. 41 depicts a cross-sectional view of the fluid collection system of FIG. 36 shown with a collection vial engaged with a shrouded cannula assembly of the plunger tube.

As shown in FIG. 41, the port 420, distal valve 421, and a portion of the inner volume 422 can define a fluid flow path that places the fluid reservoir 418 in fluid communication with the lumen-defining device. As such, the fluid reservoir 418 can be placed in fluid communication with the portion of the patient (e.g., the vein). The negative pressure within the fluid reservoir 418 produced by the movement of the plunger seal 454 can introduce a suction force within the portion of the patient. Thus, a bodily-fluid can be drawn through the port 420, the distal valve 421, and into the fluid reservoir 418. The transfer device 410 as illustrated may be useful with, for example, a CVC line, where there is little concern that the first sample will contain dermal microbes, sub-dermal microbes, contaminants, saline from a CVC line flush, heparin from a CVC line flush, or the like. The transfer device 410 may be useful where a pre-sample is not necessary or desirable, which can occur for a variety of reasons.

Figure 40:
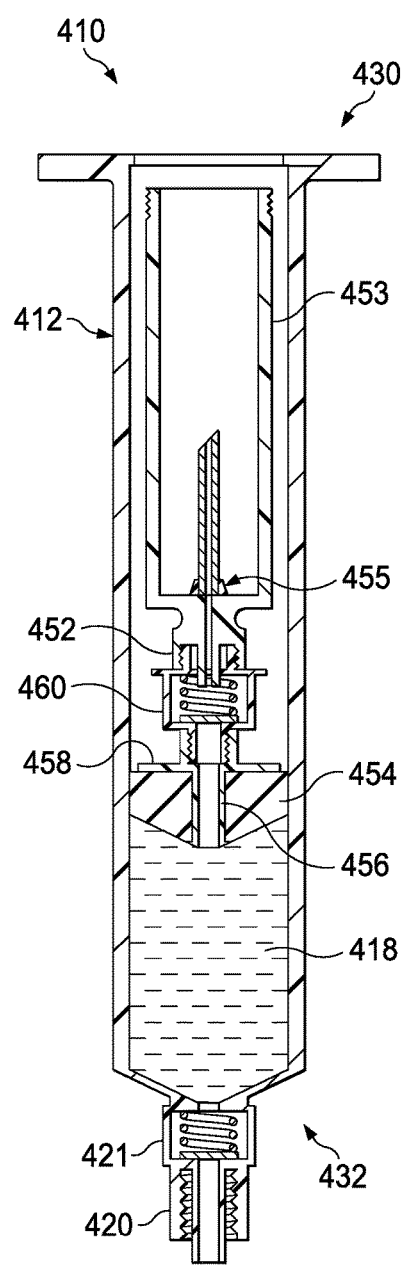
FIG. 40 depicts a cross-sectional view of the fluid collection system of FIG. 36, shown with a plunger selectively detached from a plunger tube of the actuator mechanism.
Figure 42:
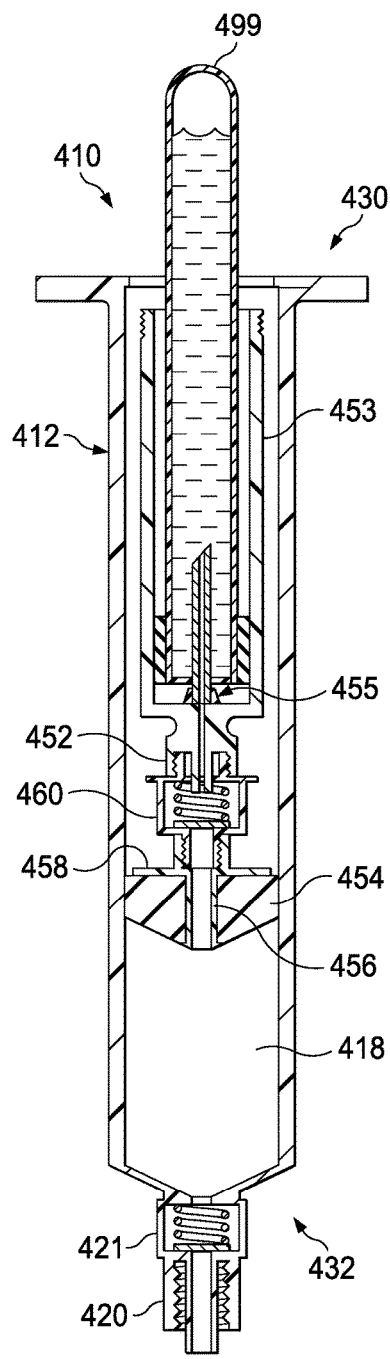
FIG. 42 depicts a cross-sectional view of the fluid collection system of FIG. 36, shown with the sample being urged from the fluid reservoir into the collection vial of FIG. 41.
Figure 43:
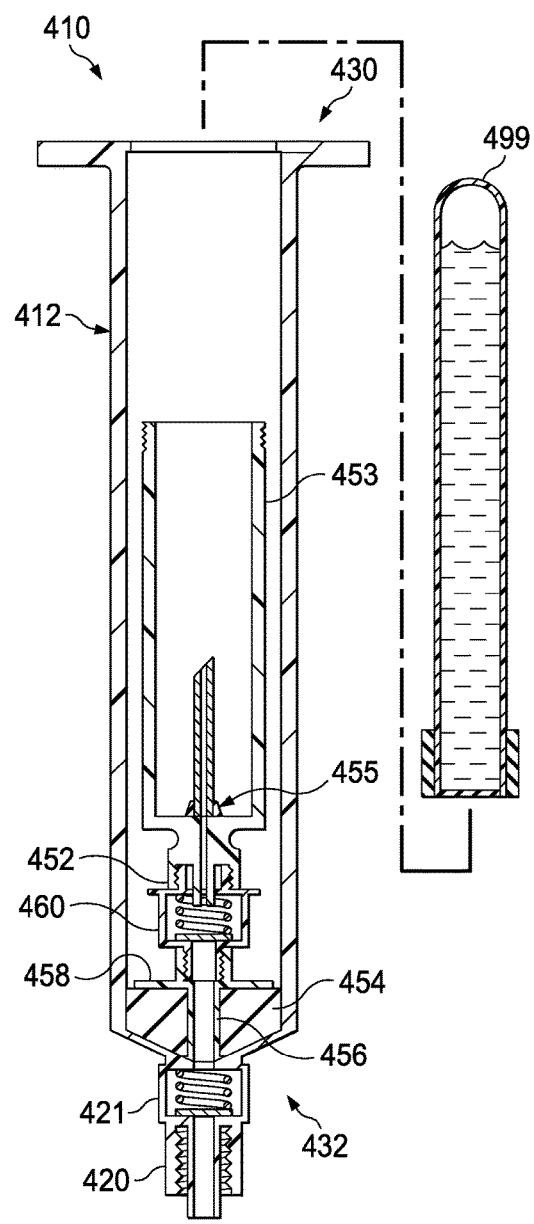
FIG. 43 depicts a cross-sectional view of the fluid collection system of FIG. 36 shown with the filled collection vial of FIG. 41 removed.

To expel fluid, the user can first disengage the plunger 444 from the plunger tube 453 such as, for example, by unthreading the plunger 444 from the plunger tube 453. Once the plunger 444 has been detached, as shown in FIG. 40, the plunger tube 453 can be accessible via an open proximal end. The shrouded cannula assembly 455 of the plunger tube 453 can now be accessed for attachment of any suitable fluid collection device such as a vacuum collection device 499. The shrouded cannula assembly 455 can be any suitable fluid transfer device or component. In one embodiment, the plunger tube 453 and the shrouded cannula assembly 455 can function in a manner substantially similar to the fluid transfer adapter 270 described with reference to FIGS. 16 and 17. The shrouded cannula assembly 455 can facilitate the transfer of the sample from the fluid reservoir 418 into a vacuum collection device 499 as shown in FIG. 42. Once the vacuum collection device 499, or the like, has been attached to the shrouded cannula assembly 455 it can be in fluid communication with the fluid reservoir 418. Negative pressure within the vacuum collection device 499 can draw the fluid sample into the vacuum collection device 499 for testing or any other suitable purposes. As shown in FIG. 43, the vacuum collection device 499 can be selective decoupled from the threaded plunger tube 453 and cannula assembly 455.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

I claim:

1. A syringe-based device for procuring bodily fluid samples comprising:
   (a) a housing including a proximal end portion and a distal end portion and defining an inner volume therebetween, the proximal end portion being open and the distal end portion having a port configured to be coupled to a lumen-defining device configured to receive bodily fluids; and
   (b) an actuator mechanism including a proximal end portion and a distal end portion, the actuator mechanism being retained at least partially within the inner volume defined by the housing and movable relative to the housing, the actuator mechanism including;
      (i) a pre-sample reservoir having a proximal end and a distal end, wherein the pre-sample reservoir is fluidically coupleable to the port and defines a first fluid reservoir;
      (ii) a plunger having a proximal end and a distal end, the distal end of the plunger being associated with the proximal end of the pre-sample reservoir such that distal movement of the plunger correspondingly moves the pre-sample reservoir distally, wherein the plunger includes at least one projection;
      (iii) a removable plunger cap, the removable plunger cap defining a cavity, wherein the plunger translates within the cavity defined by the removable plunger cap until the at least one projection engages a catch such that the removable plunger cap and the plunger are coupled when the at least one projection engages the catch;
      (iv) a plunger tube, the plunger tube being selectively engaged with the removable plunger cap, wherein the plunger tube includes a shrouded cannula assembly;
      (v) a valve, the valve being coupled with an attachment element of the plunger tube such that the valve is fluidically coupled with the shrouded cannula assembly; and
      (vi) a plunger seal, the plunger seal being coupled with the valve and plunger tube, wherein the plunger seal is movable relative to the housing to at least partially define a second fluid reservoir; and
   Wherein the actuator mechanism transitions from a first configuration in which a bodily fluid flows from the port to the first fluid reservoir, and a second configuration in which the bodily fluid flows from the port to the second fluid reservoir.

2. The syringe-based device of claim 1, wherein the housing includes a distal one-way valve positioned at about the distal end of the housing.

3. The syringe-based device of claim 1, wherein the pre-sample reservoir is a fluid collection vial having a defined volume.

4. The syringe-based device of claim 3, wherein the defined volume of the pre-sample reservoir is from about 3 ml to about 5 ml.

5. The syringe-based device of claim 1, wherein the removable plunger cap is threadedly coupled with the plunger tube.

6. The syringe-based device of claim 5, wherein threadedly decoupling the plunger cap from the plunger tube permits the pre-sample reservoir to be removed from the plunger tube.

7. The syringe-based device of claim 1, wherein the pre-sample reservoir is selectively removable from the plunger tube.

8. The syringe-based device of claim 1, further comprising a sample collection vial, wherein the sample collection vial is attached to the shrouded cannula assembly after the pre-sample reservoir is removed such that the sample collection vial draws the bodily fluid from the second fluid reservoir.

9. A syringe-based device for procuring bodily fluid samples comprising:
   (a) a housing including a proximal end portion and a distal end portion and defining an inner volume therebetween, the proximal end portion being substantially open and the distal end portion having a port configured to be coupled to a lumen-defining device for receiving bodily fluids; and
   (b) an actuator mechanism including a proximal end portion and a distal end portion, the actuator mechanism being retained at least partially within the inner volume defined by the housing and movable relative to the housing, the actuator mechanism including;
      (i) a pre-sample reservoir having a proximal end and a distal end, wherein the pre-sample reservoir defines a first fluid reservoir and is selectively detachable from the actuator mechanism;
      (ii) a plunger having a proximal end and a distal end, the distal end of the plunger being operably connected with the proximal end of the pre-sample reservoir such that distal movement of the plunger correspondingly moves the pre-sample reservoir distally;
      (iii) a removable plunger cap, the removable plunger cap defining a cavity, wherein the plunger translates within the cavity defined by the removable plunger cap;
      (iv) a plunger tube, the plunger tube being selectively engaged with the removable plunger cap, wherein the plunger tube includes a cannula assembly;
      (v) a valve, the valve being coupled with the plunger tube such that the valve is fluidically coupled with cannula assembly;
      (vi) a plunger seal, the plunger seal being coupled with the plunger tube and removable plunger cap, wherein the plunger seal is movable relative to the housing to define a second fluid reservoir; and
      (vii) a collection vial, wherein the collection vial is inserted into the plunger tube after the removal of the pre-sample reservoir such that the bodily fluid in the second fluid reservoir is collected; and
      Wherein the actuator mechanism transitions from a first configuration in which a bodily fluid flows from the port to the first fluid reservoir, and a second configuration in which the bodily fluid flows from the port to the second fluid reservoir.

10. The syringe-based device of claim 9, wherein the housing includes a distal one-way valve positioned at about the distal end of the housing.

11. The syringe-based device of claim 9, wherein the pre-sample reservoir is a fluid collection vial having a defined volume.

12. The syringe-based device of claim 11, wherein the defined volume of the pre-sample reservoir is from about 3 ml to about 5 ml.

13. The syringe-based device of claim 9, wherein the removable plunger cap is threadedly coupled with the plunger tube.

14. The syringe-based device of claim 13, wherein threadedly decoupling the plunger cap from the plunger tube permits the pre-sample reservoir to be removed from the plunger tube.

15. The syringe-based device of claim 9, wherein the pre-sample reservoir is selectively removable from the plunger tube.

16. The syringe-based device of claim 9, wherein the plunger includes a first coupling member and the removable plunger cap includes a second coupling member such that the plunger and the plunger cap are fixedly coupled with the first coupling member and the second coupling member are engaged.

17. A syringe-based device for procuring bodily fluid samples comprising:
   (a) a housing including a proximal end portion and a distal end portion and defining an inner volume therebetween, the proximal end portion being substantially open and the distal end portion having a port configured to be coupled to a lumen-defining device for receiving bodily fluids; and
   (b) an actuator mechanism including a proximal end portion and a distal end portion, the actuator mechanism being retained at least partially within the inner volume defined by the housing and movable relative to the housing, the actuator mechanism including;
      (i) a pre-sample reservoir having a proximal end and a distal end, wherein the pre-sample reservoir defines a first fluid reservoir and is selectively detachable from the actuator mechanism;
      (ii) a plunger having a proximal end and a distal end, the distal end of the plunger being operably connected with the proximal end of the pre-sample reservoir such that distal movement of the plunger correspondingly moves the pre-sample reservoir distally;
      (iii) a plunger cap, wherein the plunger translates relative to the plunger cap;
      (iv) a plunger tube, the plunger tube being selectively engaged with the plunger cap, wherein the plunger tube includes a cannula;
      (v) a valve, the valve being associated with the plunger tube such that the valve is fluidically coupled with cannula;
      (vi) a plunger seal, the plunger seal being coupled with the plunger tube and plunger cap, wherein the plunger seal is movable relative to the housing to define a second fluid reservoir; and
      (vii) a collection vial, wherein the collection vial is inserted into the plunger tube after the removal of the pre-sample reservoir such that the bodily fluid in the second fluid reservoir is collected; and Wherein the actuator mechanism transitions from a first configuration in which a bodily fluid flows from the port to the pre-sample reservoir, a second configuration in which the bodily fluid flows from the port to the second fluid reservoir, a third configuration in which the pre-sample reservoir is removed, and a fourth configuration in which the collection vial is coupled with the cannula such that the bodily fluid flows from the second fluid reservoir into the collection vial.

18. The syringe-based device of claim 17, wherein the housing includes a distal one-way valve positioned at about the distal end of the housing.

19. The syringe-based device of claim 17, wherein the pre-sample reservoir is a fluid collection vial having a defined volume of from about 3 ml to about 5 ml.

20. The syringe-based device of claim 17, wherein the plunger includes a first coupling member and the removable plunger cap includes a second coupling member such that the plunger and the plunger cap are fixedly coupled with the first coupling member and the second coupling member are engaged.

* * * * *